(12) United States Patent
Beech, Jr. et al.

(10) Patent No.: US 7,223,714 B2
(45) Date of Patent: *May 29, 2007

(54) METHOD OF TRANSFERRING CATALYST IN A REACTION SYSTEM

(75) Inventors: James H. Beech, Jr., Kingwood, TX (US); Neil Vaughn Stephen, Kingwood, TX (US); Teng Xu, Houston, TX (US); Luc R. M. Martens, Meise (BE); Richard E. Walter, Long Valley, NJ (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 10/981,269

(22) Filed: Nov. 4, 2004

(65) Prior Publication Data

US 2006/0094593 A1    May 4, 2006

(51) Int. Cl.
*B01J 27/182* (2006.01)
(52) U.S. Cl. ............... 502/214; 502/208; 502/209; 502/210; 502/211; 502/213
(58) Field of Classification Search ............ 502/208, 502/209, 210, 211, 213, 214
See application file for complete search history.

(56) References Cited

U.S. PATENT DOCUMENTS

| | | | | |
|---|---|---|---|---|
| 4,764,269 A | | 8/1988 | Edwards et al. ............ 208/120 |
| 4,990,314 A | * | 2/1991 | Herbst et al. ............... 422/144 |
| 5,939,597 A | * | 8/1999 | Dessau et al. .............. 585/447 |
| 5,965,474 A | * | 10/1999 | Balko et al. ................. 502/65 |
| 6,316,683 B1 | | 11/2001 | Janssen et al. .............. 585/640 |
| 6,512,155 B1 | * | 1/2003 | Johnson et al. ............. 585/481 |
| 6,897,179 B2 | * | 5/2005 | Fung et al. ................. 502/208 |
| 2003/0004056 A1 | | 1/2003 | Mees et al. ................. 502/208 |
| 2003/0055304 A1 | * | 3/2003 | Fung et al. ................. 585/640 |
| 2003/0163010 A1 | * | 8/2003 | Xu et al. .................... 585/638 |

OTHER PUBLICATIONS

Mees et al, "*Improvement of the Hydrothermal Stability of SAPO-34*", Chem. Commun., 2003, (1), 44-45, no month available.

* cited by examiner

*Primary Examiner*—Elizabeth D. Wood

(57) ABSTRACT

The invention is directed to methods of transfering catalyst particles into and within reaction systems. The reaction systems are those that use catalysts that comprise molecular sieves, particularly metalloaluminophosphate molecular sieves, especially metalloaluminophosphate molecular sieves which are susceptible to loss of catalytic activity due to contact with water molecules. The transfer methods provide appropriate mechanisms for transporting catalyst into and within a reactor to protect against loss of catalytic activity that can occur due to contact with water molecules.

27 Claims, 8 Drawing Sheets

METHOD OF TRANSFERRING CATALYST IN A REACTION SYSTEM

FIELD OF THE INVENTION

This invention relates to processes or methods of adding and moving solid catalyst particles within a reaction system. In particular, this invention relates to processes or methods of adding, moving, and removing solid catalyst particles within reaction systems while maintaining or protecting the catalytic activity of molecular sieves that are susceptible to loss of catalytic activity due to contact with water molecules.

BACKGROUND OF THE INVENTION

Molecular sieves are generally derived from alumina silicate materials and contain a pore system, which is a network of uniform pores and empty cavities. These pores and cavities catch molecules that have a size equal to or less than the size of the pores and cavities, and repel molecules of a larger size.

The pores and cavities of molecular sieves are formed as a result of adding template materials during the molecular sieve manufacturing process. During the formation of the molecular sieves themselves, a lattice type chemical structure is formed from the alumina silicate type materials. This lattice type structure essentially wraps around the template material, with the template material acting as a means of forming the pore structure within the molecular sieve. The resulting molecular sieve may be combined with other components for the benefit of adjusting various properties of the molecular sieve or to form larger particles.

To make the molecular sieve suitable for use, the template must be removed so that the pores and cavities are open to catch molecules, either for the purpose of adsorbing the molecules from the environment or to react the molecules to form a desired product. The reaction occurs when the molecules come into contact with catalytic sites located within the pore system, particularly within one or more of the empty cavities or cages as sometimes called.

The template is conventionally removed from the molecular sieve by calcining or burning out the template. An elution process can also be used to remove the template, although calcination is preferred. Once the template is removed, the molecular sieve is considered to be activated or ready for use. The activated molecular sieve has its pore system, including the empty cavities or cages open to the immediate environment, and ready for use.

Activated metalloaluminophosphate molecular sieves that have catalytic sites within their microporous structure, e.g., silicoaluminophosphate (SAPO) molecular sieves, have been found to be sensitive to moisture. In general, significant exposure of the activated molecular sieves to moisture has been found to deactivate the catalytic activity of the molecular sieves. Unfortunately, methods of protecting activated metalloaluminophosphate molecular sieves against the harmful effects of moisture are limited.

U.S. Pat. No. 6,316,683 B1 (Janssen et al.) discloses a method of protecting catalytic activity of a SAPO molecular sieve by shielding the internal active sites of the molecular sieve from contact with moisture. The template itself can serve as the shield, or an anhydrous blanket can serve as a shield for an activated sieve that does not include template. It is desirable to shield the active sites, because activated SAPO molecular sieves will exhibit a loss of catalytic activity when exposed to moisture.

U.S. Pat. No. 4,764,269 (Edwards et al.) discloses a method of protecting SAPO-37 catalyst from deactivating as a result of contact with moisture. The catalyst is maintained under storage conditions such that the organic template component of the molecular sieve is retained in the SAPO-37 molecular sieve, until such time as the catalyst is placed into a catalytic cracking unit. When the catalyst is exposed to the FCC reaction conditions, wherein the reactor is operated at 400° to 600° C. and the regenerator operated at about 600° to 850° C., the organic template is removed from the molecular sieve pore structure, and the catalyst becomes activated for the cracking of hydrocarbons. According to this procedure, there is little if any contact with moisture.

Mees et al., "Improvement of the Hydrothermal Stability of SAPO-34," Chem. Commun., 2003, (1), 44-45, first published as an advance article on the web Nov. 22, 2002, discloses a method of protecting SAPO-34 molecular sieve, based on a reversible reaction of NH3 with acid sites of the sieve. The method transforms a H+-SAPO-34 into an NH4+-SAPO-34 in reversible way. The NH4+-SAPO-34 is said to be able to withstand severe steaming for an extended period of time without loss of structural integrity and acidity.

As new large scale, commercial production facilities, which use molecular sieves in the production process, continue to be implemented, protecting the activated molecular sieves from loss of catalytic activity as a result of contact with moisture continues to become an even greater challenge. What is needed are additional methods for reducing the exposure of catalyst particles to water molecules, so that the amount of water vapor that comes into contact with catalyst particles is controlled and minimized throughout the reaction system.

SUMMARY OF THE INVENTION

In one aspect, this invention provides methods that assist in the protection of molecular sieves against loss of catalytic activity during addition, storage, and transport of catalyst particles to and from a reaction system.

In an embodiment, the invention provides a process for transferring catalyst particles into a oxygenate to olefin reaction system. The process includes storing metalloaluminophosphate catalyst particles in a container, transferring the stored particles from the container into a reaction system, and introducing a gas flow into the container during the catalyst particle transfer, where the volume of gas introduced into the container during transfer is comparable in volume to the volume of catalyst plus gas exiting the container through a catalyst particle exit.

In another embodiment, the cumulative moisture content of any gases introduced into the storage container or used for transfer of the stored particles is controlled to be less than 0.1 lb water per lb of catalyst transferred. One way of controlling the moisture content is by controlling the dew point of the gases introduced into the storage container or used for transfer of the stored particles.

In still another embodiment, the catalyst particles can be first transferred into an intermediate hopper, such as a feeder hopper. The catalyst particles are then maintained in the intermediate hopper prior to being moved into the reaction system.

BRIEF DESCRIPTION OF THE DRAWINGS

Examples of various embodiments of this invention are shown in the attached Figures, wherein.

DETAILED DESCRIPTION OF THE INVENTION

Figure 1:
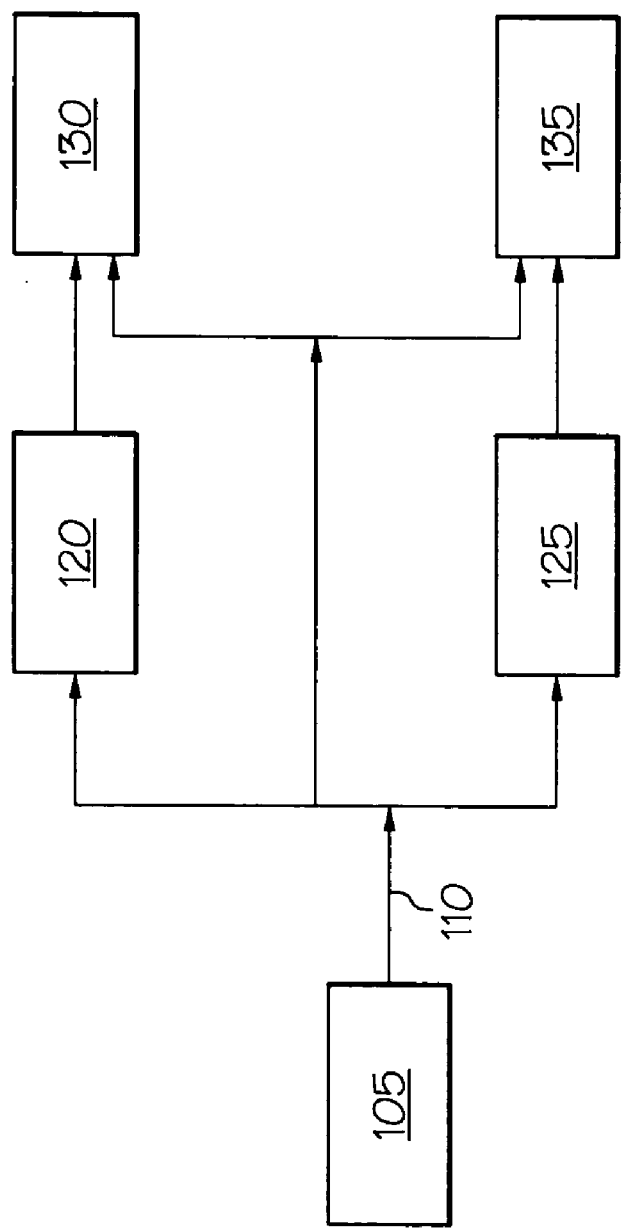
FIG. 1 is a schematic overview of a system for transferring catalyst particles to and from a reaction system according to an embodiment of the invention.

I. Transfer Methods to Protect Against Loss of Catalytic Activity

This invention is directed to methods of adding, storing, and moving catalyst particles to and from reaction systems that use catalysts that comprise molecular sieves, particularly metalloaluminophosphate molecular sieves, which are susceptible to loss of catalytic activity due to contact with water molecules. Since many metalloaluminophosphate molecular sieves, particularly silicoaluminophosphate molecular sieves, are susceptible to loss of catalytic activity upon activation and contact with water molecules, the environment of the catalyst particles should be controlled to minimize contact with moisture whenever possible. If activated catalyst is left exposed to water vapor for even short periods of time, a significant loss of catalytic activity can occur.

According to various embodiments of this invention, the exposure of solid catalyst particles to moisture is minimized during the addition, storage, and movement of particles to and from a reaction system. This is achieved in part by reducing the amount of gas flow the catalyst particles are exposed to. Because any gas flow can contain some moisture, reducing the amount of moisture containing gas flow and/or reducing the amount of moisture in the gas flow will reduce the risk that the catalyst particles will adsorb water molecules from the gas flow.

In an embodiment, during addition of catalyst particles to the reaction system, the exposure to moisture is reduced by reducing the rate of gas flow and/or reducing the moisture content of the gas flow during the particle addition process. During transport and storage, the transport and storage container can contain catalyst particles and some amount of gas, such as a stagnant blanket of inert gas. During storage the container is sealed and no aeration gas flow is used to prevent moisture from entering. The amount of gas in the storage container is sufficient to support a desired pressure in the storage container. For example, in many embodiments the particles will be transported and stored in the storage container at a pressure of up to 15 psig. In such embodiments, an inert gas can be used to pressurize the container to up to 15 psig. In other embodiments, the particles can be transported at standard pressure.

When particles are transferred from the storage container to the reaction system, a volume corresponding to the volume of transferred particles is removed from the storage container. If a gas flow is not added to the storage container during transfer, the loss of the transferred particle volume will cause any gas in the storage container to expand, leading to a reduction in pressure in the storage container. As more particles are transferred, the lowering of pressure in the storage container can impact the transfer rate for various reasons, such as having a lower pressure in the storage container than in the reaction system.

To prevent pressure loss in the storage container, a gas flow can be introduced into the storage container during particle transfer. In an embodiment, the volume rate of gas flow is selected to displace a volume similar to the volume of particles being transferred into the reaction system. In another embodiment, the gas flow can be introduced into the storage container via multiple entry points. Selecting a volume rate of gas flow that corresponds to the lost volume of transferred particles allows the pressure in the storage container to be maintained at a roughly constant value during a transfer process without exposing the catalyst particles to unnecessary gas flow that may contain moisture. This gas flow can also assist in fluidizing the catalyst particles as the particles leave the storage container, thus allowing the catalyst particles to flow more freely.

The amount of gas flow entering the storage container can be expressed as a volume ratio relative to the volume of catalyst particles and gas leaving the storage container via a catalyst outlet. In determining the volume ratio, the volume of gas entering and exiting the storage container is measured at the pressure of the container at the beginning of a catalyst transfer operation. In an embodiment, the volume transfer ratio of gas entering the storage container versus catalyst particles and gas exiting from the storage container via a catalyst outlet is 10.0 or less, or 5.0 or less, or 2.0 or less, or 1.5 or less, or 1.2 or less, or 1.1 or less. In another embodiment, the volume transfer ratio of gas entering the storage container versus catalyst particles and gas exiting from the storage container via a catalyst outlet is at least 0.99, or at least 1.0, or at least 1.1. When the volume transfer ratio of gas entering the storage container versus catalyst particles and gas exiting the catalyst outlet from the storage container are greater than 1.0, the excess gas is vented from the container via a pressure control valve in order to maintain a constant pressure. However, if the transfer ratio is less than 1.0, the pressure of the container will decline which could limit the catalyst flow rate out of the storage container.

The amount of moisture that catalyst particles are exposed to during a catalyst transfer operation can also be controlled. In an embodiment, during a catalyst transfer operation, the cumulative moisture content of the gases used in aerating the storage container and for pneumatically transferring the catalyst is 0.1 lb total water/lb of total catalyst or less, or 0.01 lb total water/lb of total catalyst or less, or 0.001 lb total water/lb of total catalyst or less, or 0.0001 lb total water/lb of total catalyst or less. The catalyst transfer is preferably controlled so that the water content of the catalyst is maintained at the predetermined or desired amount during transfer as well as after transfer is complete, such as during any subsequent storage.

In another embodiment, the cumulative moisture content targets can be advantageously reached by controlling the atmospheric pressure water dew point of the supply source for the aeration and transfer gas. In an embodiment, the dew point of the aeration and transfer gas has a dew point of less than 100° F., or less than 40° F., or less than 0° F., or less than −40° F. to limit the exposure of the catalyst to water during transfer.

In an embodiment, the supply gas used to pneumatically convey the catalyst in a conduit from the storage container to an intermediate hopper or to the reactor system is flowed at a rate of at least 0.01 scf/lb catalyst, or at least 0.1 scf/lb catalyst, or at least 0.2 scf/lb catalyst, or at least 0.5 scf/lb catalyst. In another embodiment, the supply gas is flowed at a rate of 5.0 scf/lb catalyst or less, or 2.0 scf/lb catalyst or less, or 1.0 scf/lb catalyst or less, or 0.75 scf/lb catalyst or less.

In another embodiment, this invention provides a method for storing and transferring catalyst particles to and from a reaction system. New catalyst particles added to a reaction system are often stored in an intermediate hopper until the particles are needed to replace particles losses. In various embodiments of this invention, the gas flow in the intermediate hopper is turned off during storage of particles in the intermediate hopper. In such embodiments, the gas flow in the intermediate hopper is only turned on when catalyst particles are transferred from the intermediate hopper to replace particles lost during processing in the reaction system.

In yet another embodiment, this invention provides an overall method for transferring catalyst particles to and from a reaction system. The method provides for control of the environment for a catalyst particle from the time of synthesis to the time for use of the catalyst in a reactor. By maintaining control over the moisture that the catalyst particles are exposed to, the catalyst particles will have a higher activity and/or a longer remaining effective lifetime upon entering a reactor.

II. Initial Transfer of Catalyst into Reaction System

Control over moisture content begins when the catalyst particles are synthesized. During synthesis, catalyst particles are protected against moisture absorption by a template compound in the particle. This template must be removed to activate the catalyst. However, removing the template also makes the catalyst particles susceptible to deactivation due to water absorption.

Because of the possibility of deactivation due to exposure to water, the atmosphere surrounding the catalyst particles should be controlled during transport of the particles to the reaction system. Several types of containers are currently available for transporting catalyst particles, such as rail hoppers, truck hoppers, bulk containers, bins, and sacks. The various types of transport containers can carry as much as 1-100 tons of catalyst and are made of various materials ranging from metals such as steel to woven polypropylene sacks with inner liners of a polymeric material such as Valeron or other liners such as metal containing foils. Many of these containers can also be pressurized relative to the outside atmosphere. Pressurizing the container reduces or eliminates the likelihood that water vapor can diffuse into the container and deactivate the catalyst particles. In an embodiment, containers not employing polymer linings are preferred, as the polymer linings can be susceptible to varying degrees of moisture permeation over time while the metal storage containers generally have no water permeability.

In another embodiment of the invention, the container for storage or transport provides an anhydrous environment for the catalyst containing the activated sieve. Such an environment can be provided by covering the activated sieve loaded into a container with a gas or liquid blanket under anhydrous conditions. As provided herein, the anhydrous gas or liquid blanket will have no more than a limited amount of water. The anhydrous gas blanket can be provided under vacuum conditions or under atmospheric or greater pressure conditions. In an embodiment, the anhydrous gas blanket has a water content of about 10 volume percent water or less, or 1.0 volume percent water or less, or 0.1 volume percent water or less, or 0.01 volume percent water or less. In another embodiment, the anhydrous liquid blanket will desirably have a water content of not greater than about 200 ppm water, preferably not greater than about 100 ppm water, and more preferably not greater than about 50 ppm water. The anhydrous environment can be applied during storage, transport or loading of the activated catalyst.

The anhydrous gas blanket is a gas under standard temperature and pressure conditions and does not react to any significant degree with the molecular sieve structure. The gas is preferably composed of at least one gas selected from the group consisting of nitrogen, helium, CO, $CO_2$, $H_2$, argon, $O_2$, light alkanes (especially $C_1$-$C_4$ alkanes, particularly methane and ethane), and cyclo-alkanes. The gas blanket can be maintained at any pressure, including under vacuum or at pressures above standard, even if the gas becomes liquid at pressures above standard, as long as the conditions remain anhydrous. In some embodiments, non-combustible gases such as nitrogen, air, helium, argon, and other inert gases are preferred for forming the anhydrous gas blanket. When catalyst particles are transferred directly from a container with an anhydrous gas blanket to a regenerator, using nitrogen, air, or an inert gas as the gas blanket reduces the risk that an explosion hazard environment will form in the regenerator.

The anhydrous liquid blanket is a liquid under standard temperature and pressure conditions, and does not react to any significant degree with the molecular sieve structure. The liquid is preferably at least one liquid composition selected from the group consisting of alkanes, cyclo-alkanes, $C_6$-$C_{30}$ aromatics, and alcohols, particularly $C_4$+ branched alcohols.

After transporting the catalyst particles to the desired reaction system, the catalyst must be added into the system. Preferably, the catalyst particles are transferred into the reaction system using a closed system. For example, the catalyst particles can be transferred into the reaction system by forming a sealed conduit between the transport container and the reaction system. In an embodiment, transfer of the particles begins by opening a valve at the bottom of the transport container. In an embodiment, the particles are pulled out of the transport container due to gravity. In another embodiment, the container is pressurized so that the flow of the particles is assisted by a pressure differential between the container and the destination of the particles.

Catalyst particles exiting the transport container enter a conduit. This conduit is connected to a source of pressurized gas. The pressurized gas pneumatically conveys the catalyst particles through the conduit and into the reactor, the regenerator, an intermediate hopper, or another container within the reaction system. In some embodiments, the particles can be first transferred into an intermediate hopper and then dropped out of the intermediate hopper into another conduit for transfer to the reactor or regenerator. The source container is operated generally at a 5-10 psig higher pressure than the destination container to assist in catalyst flow and avoid backflow. Valves are placed in the transfer conduits near the catalyst source and destination container or vessel so the container or vessel can be isolated once the catalyst transfer has been completed. Valves are also included where the aeration and transport gas enters the system at the catalyst source vessel or container.

FIG. 1 provides a schematic overview of a system for transfering catalyst particles into a reaction system. Storage container 105 represents a container suitable for transporting catalyst particles to the location of the reaction system. Catalyst particles can be transferred from the storage container into the system via one or more conduits 110. As shown in FIG. 1, the conduits can connect the storage container to one or more intermediate hoppers 120, 125 in the reaction system. Catalyst particles transferred into these intermediate hoppers can then be added to the reactor 130 or regenerator 135 as desired. Alternatively, a conduit 110 can directly connect the storage container 105 with either reactor 130 or regenerator 135.

Figure 2:
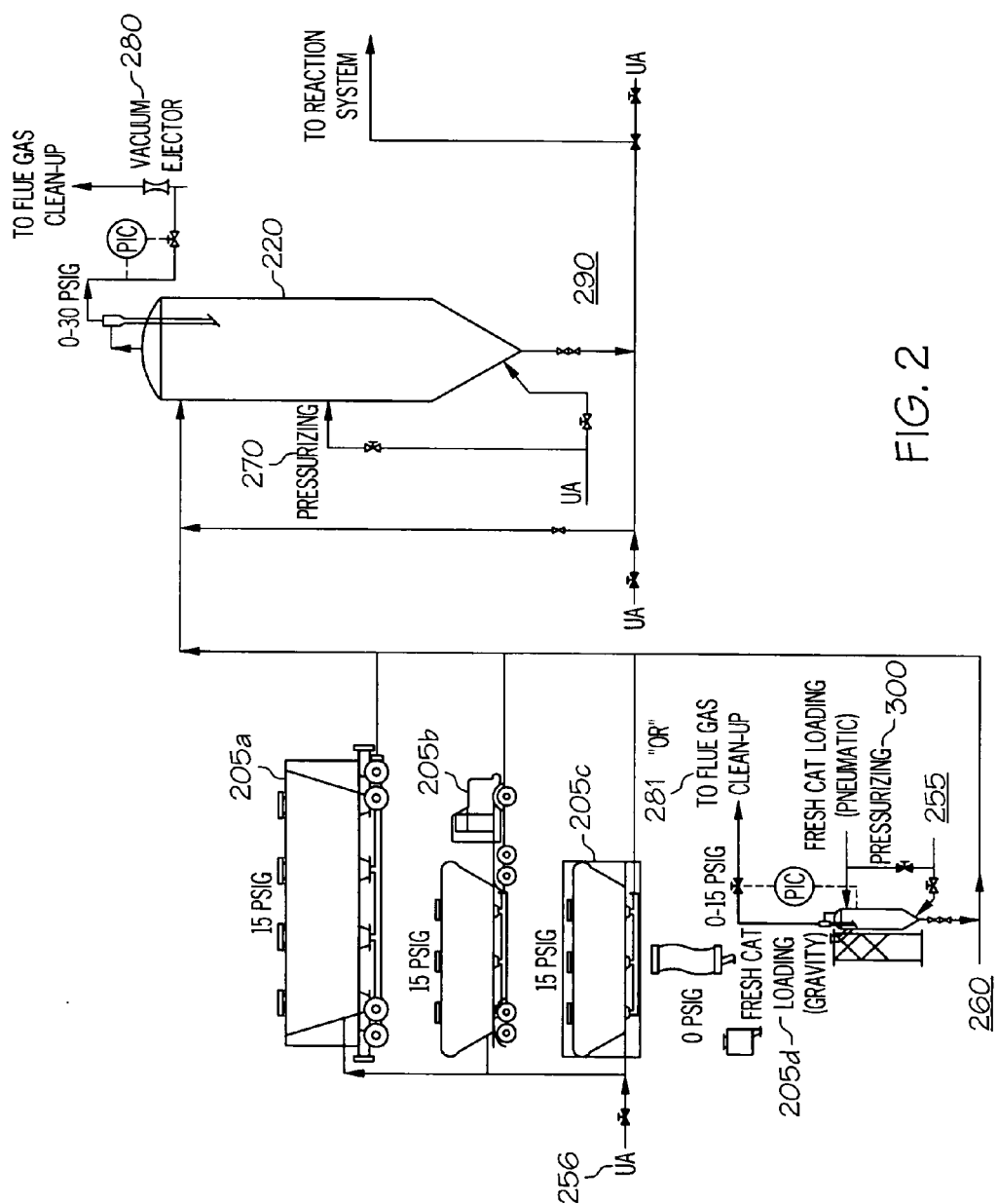
FIG. 2 is a schematic overview of a system for transferring catalyst particles into a reaction system according to an embodiment of the invention.

FIG. 2 schematically shows a system for transferring catalyst particles from a transport or storage container into a reaction system. The catalyst particles are brought to the reaction system in one or more storage containers 205. FIG. 2 shows several examples of possible delivery or storage containers 205a-d, including rail hopper 205a, truck hopper 205b, container 205c, and sacks or bins 205d. In various embodiments, the hoppers, containers, sacks, and bins can be of any convenient size, including vessels that hold up to 100 tons or more of catalyst particles. Alternatively, smaller hoppers, containers, sacks and bins that hold 5 tons or less of catalyst particles can also be used. During transfer, a gas flow is introduced into a container 205, such as a gas flow introduced into container 205a from gas source 256. The gas flow assists the particles in flowing out of the storage container or feeder hopper. After the particles exit the storage container or feeder, the particles are propelled by a second gas flow from a gas source 256 or 260 toward a vessel in the reaction system. In FIG. 2, the catalyst particles are being transferred into an intermediate hopper 220. An "e-cat" or equilibrium catalyst hopper is shown in FIG. 2. Other larger or smaller types of hoppers could also serve as the intermediate hopper. Alternatively, catalyst particles in 5 ton or smaller sacks or bins 205d can be gravity fed directly into another intermediate hopper, such as feeder hopper 300. The catalyst is then transferred generally at higher pressures from the intermediate hopper, which can contain up to a full reaction system inventory of catalyst, directly into a processing chamber in the reaction system, such as a reactor (not shown) or regenerator. The intermediate hopper 220 or 300 is equipped with a pressurizing system 270 to control the pressure within the intermediate hopper. The intermediate hopper also includes a release conduit 280 or 281 to exhaust any gas displaced when catalyst particles are added to the intermediate hopper and to control the intermediate hopper pressure. The intermediate hopper further includes an exit conduit 290. The exit conduit allows catalyst particles in the intermediate hopper to be transferred to other parts of the reaction system, such as the reactor or regenerator.

One method of starting a transfer process is to open a valve in the bottom of a location that currently contains catalyst particles, such as a intermediate hopper or a storage container. The particles will fall through the valve into a conduit. Gas is then flowed through the conduit to propel the catalyst particles toward their destination.

In an alternative embodiment, the catalyst particles can be transferred into the reaction system by an open connection, where the catalyst particles are briefly exposed to an outside atmosphere during transfer from the transport container to the reaction system. For example, particles could be poured into an intermediate hopper, such as a feeder hopper. Preferably, if the particles are exposed to an outside atmosphere, the outside atmosphere should have as little water content as possible.

In an embodiment where a reaction system is going through a start-up procedure, newly added catalyst particles are passed into the regenerator prior to beginning the MTO reaction. In another embodiment, the particles are transferred to the regenerator after first passing through a hopper or other storage container within the reaction system, such as the equilibrium or e-cat hopper. In still another embodiment, catalyst particles can be passed directly into the reactor without entering the regenerator.

III. Transfer of Catalyst to a Reaction System During Normal Operation

After start-up of the reaction system, the nature of the MTO reaction leads to a loss of catalyst particles. The particles can be lost for various reasons. For example, particles can be lost due to attrition, such as by breaking into small particles; due to inefficient separation, such as loss of particles with a product outflow; or due to intentional removal when a sample of deactivated catalyst particles is found within the system. Regardless of the cause, when catalyst particle losses occur, additional particles are added back into the system.

In an embodiment, additional particles are added into the system directly from a storage container into a processing chamber such as a reactor or a regenerator. In another embodiment, additional particles are added into the system via one or more intermediate hoppers within the reaction system. After start-up, an intermediate hopper (such as a feeder hopper) can be filled with catalyst particles. As particle losses occur, fresh catalyst particles can be drawn from the intermediate hopper into the reactor or regenerator. Adding particles from a transport or storage container to the intermediate hopper can occur by any suitable method, including the transfer methods previously described. In an embodiment, the use of the intermediate hopper is preferred when the transport or storage container cannot be pressurized to pressures greater than the reaction system pressure. In such an embodiment, the intermediate hopper can be filled with catalyst at some lower pressure compatible with the catalyst storage container pressure capability. The pressure in the intermediate hopper can then be increased to be compatible with catalyst transfer to the reaction system.

In an embodiment, catalyst particles are added to a reaction system from an intermediate hopper by first opening a valve at the bottom of the intermediate hopper. This allows catalyst particles to fall into a conduit, where the particles can be blown through the conduit and into the reactor or regenerator as desired. During this addition, a flow of gas is added to the intermediate hopper. As described above with regard to storage containers, the minimum volume flow requirement for the gas flow into the intermediate hopper during catalyst transfer is comparable to the volume rate at which catalyst is exiting the intermediate hopper. The volume flow of gas entering the intermediate hopper can be characterized by a volume transfer ratio relative to the volume of catalyst particles and gas exiting the intermediate hopper via the catalyst outlet. In an embodiment, the volume transfer ratio of gas entering the storage container versus catalyst particles and gas exiting from the storage container via a catalyst outlet is 10.0 or less, or 5.0 or less, or 2.0 or less, or 1.5 or less, or 1.2 or less, or 1.1 or less. In another embodiment, the volume transfer ratio of gas entering the storage container versus catalyst particles and gas exiting from the storage container via a catalyst outlet is at least 0.99, or at least 1.0, or at least 1.1. As described above, in determining the volume ratio, the volume of gas entering and exiting the storage container is measured at the pressure of the container at the beginning of a catalyst transfer operation.

In still another embodiment, when particles are not being transferred out of the intermediate hopper, the flow of gas in the intermediate hopper is turned off. This further reduces the amount of water the catalyst particles are exposed to.

IV. Detecting Molecular Sieve Acid Density

In an embodiment the invention also provides a method for detecting the catalytic activity of some types of catalyst particles within a reaction system. In methanol-to-olefin reactions as well as other reaction systems, H-SAPO-34 is a preferred catalyst. The reaction for converting methanol to olefins using H-SAPO-34 is an acid-catalyzed reaction. Thus, the acid density of H-SAPO-34 plays a role in determining the activity of the catalyst and the selectivity of a methanol-to-olefin process. The acid density of H-SAPO-34 with little or no water contamination can be at least 0.35 mmol/gram, or at least 0.40 mmol/gram. If deactivated by water, the acid density of H-SAPO-34 can drop to less than 0.25 mmol/gram, or less than 0.20 mmol/gram.

In an embodiment, this invention provides a method for nearly real-time monitoring of the acid density on catalyst particles such as H-SAPO-34 particles. The acid density is measured using Fourier Transform Infrared (FT-IR) spectroscopy. Using FT-IR spectroscopy, the acid density of H-SAPO-34 catalyst particles can be measured within about one hour, and often in less than 30 minutes.

In an embodiment, Diffuse Reflectance Fourier Transform Infrared spectroscopy is performed using an FT-IR spectrometer and a high temperature, high pressure diffuse reflectance chamber. The collected spectra can be processed to quantify the peak area for the acid sites. After importing the spectra into a commercial software program for peak integration (PeakSolve), the spectra can be corrected with multi-point baseline correction. The baseline corrected spectra are then integrated following deconvolution of the spectra.

In the above embodiment, a high temperature diffuse reflectance cell was used for the FT-IR measurements. In other embodiments, other types of infrared spectroscopy cells or other optical probes can be used to detect water adsorption on catalyst particles. For example, a transmission cell could be used for infrared spectroscopy measurements. In another embodiment, a fiber-optic probe could be used to perform in-situ monitoring of acid density on catalyst particles. This type of embodiment can be used for monitoring of acid density of catalyst particles during periods of storage or transport. A fiber-optic probe could be permanently located in a storage vessel, or the probe could be movable between one or more insertion points in the storage vessel. This type of embodiment allows for real-time or nearly real-time monitoring of the catalyst particles.

In an embodiment, the water content on H-SAPO-34 catalyst particles is monitored by monitoring adsorption wavelengths that are known to change after water adsorption. For example, a sample of H-SAPO-34 exposed to moisture will show an additional broad band peak centered around 2910 $cm^{-1}$. This peak is characteristic of water molecules that are hydrogen bonded to Bronsted acid sites, such as the acid sites present on H-SAPO-34 catalyst particles. In another embodiment, the acid density of H-SAPO-34 catalyst particles is monitored by monitoring the integrated peak area for peaks at wavenumbers of 3592 and 3620 $cm^{-1}$. These adsorptions correspond to adsorptions at acid sites on the catalyst. In still other embodiments, other spectral peaks can be used to track the presence of moisture on H-SAPO-34 catalyst particles.

In still another embodiment, a transfer pipe for transferring catalyst particles within a reaction system can be monitored by FT-IR to determine the acid density and moisture content of catalyst particles within the reaction system. For example, an FT-IR apparatus using fiber-optic probes could be configured to take spectra of catalyst particles being transferred from an intermediate hopper to a reactor or regenerator in a reaction system. FT-IR spectra of the particles could then be obtained during transfer from the intermediate hopper to the reactor or regenerator. If the particles have low acid density/moisture contamination, the transfer could be stopped to prevent adding the deactivated catalyst to the reactor. For example, if the acid density is less than 0.25 mmol/gram, or less than 0.20 mmol/gram, the transfer could be stopped. In still another embodiment, an FT-IR apparatus could be used to monitor catalyst particles during or after synthesis of the formulated catalyst particles. For example, after "calcining" catalyst particles to remove any template molecules, the catalyst particles could be measured to verify the acid density and/or the moisture content of the particles. If the particles show an acid density or moisture content outside of acceptable ranges, the production process for the particles can be stopped or modified to minimize the production of inferior catalyst particles.

Figure 4:
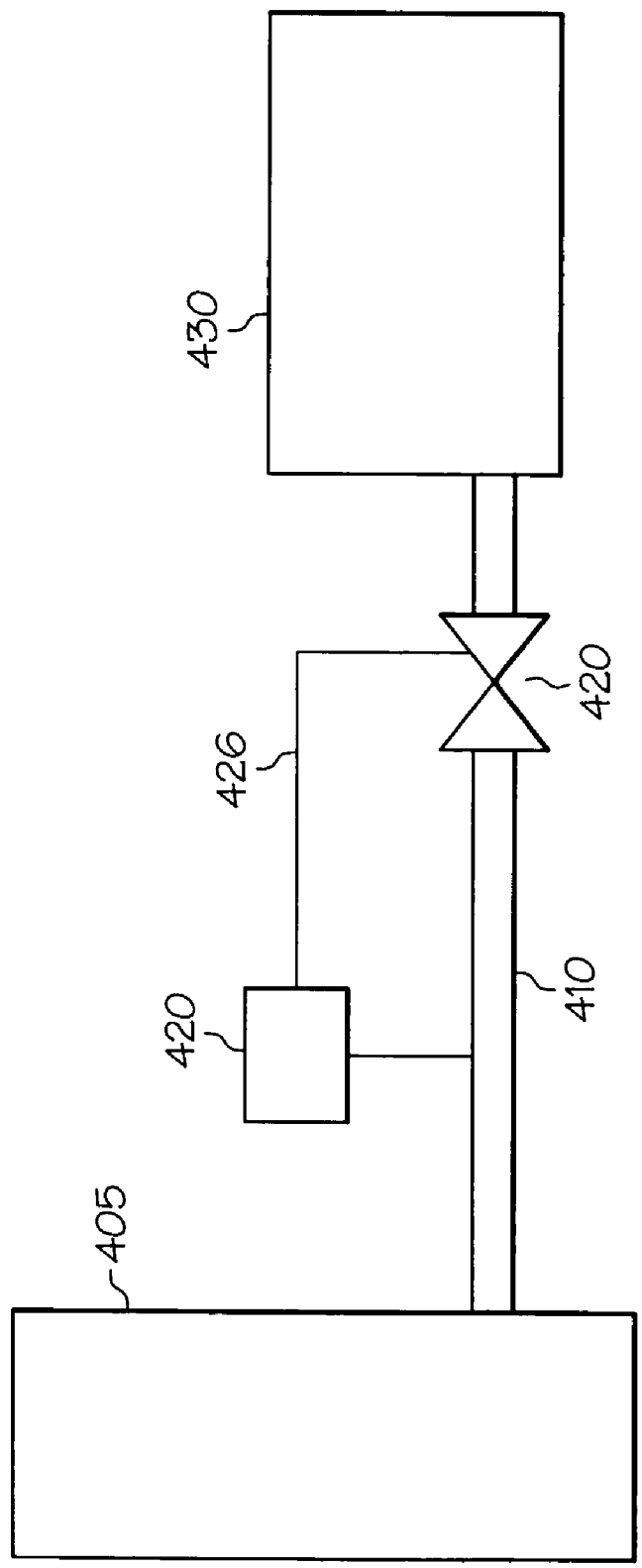
FIG. 4 schematically shows an apparatus for acquiring FT-IR spectra of catalyst particles in a reaction system according to an embodiment of the invention.

FIG. 4 schematically shows a system for measuring acid density/water content on catalyst particles in a reaction system according to an embodiment of the invention. In FIG. 4, catalyst particles are stored in a storage container or intermediate hopper 405 for future use in a reaction system. When it is desired to add catalyst particles to reactor 430 (or alternatively to the regenerator), catalyst particles exit the intermediate hopper 405 and enter transfer conduit 410. As the particles move through transfer conduit 410, FTIR device 420 acquires spectroscopic data about the water content or acid density of the catalyst particles. If the spectroscopic data indicates that the catalyst particles are undesirable due to deactivation or high water content, valve 425 can be closed to prevent further particle transfer. In the embodiment shown in FIG. 4, valve 425 is operatively connected 426 to FTIR device 420 to allow for automatic closure of the valve upon detection of undesirable catalyst particles.

V. Additional Embodiments of the Invention

Figure 3:
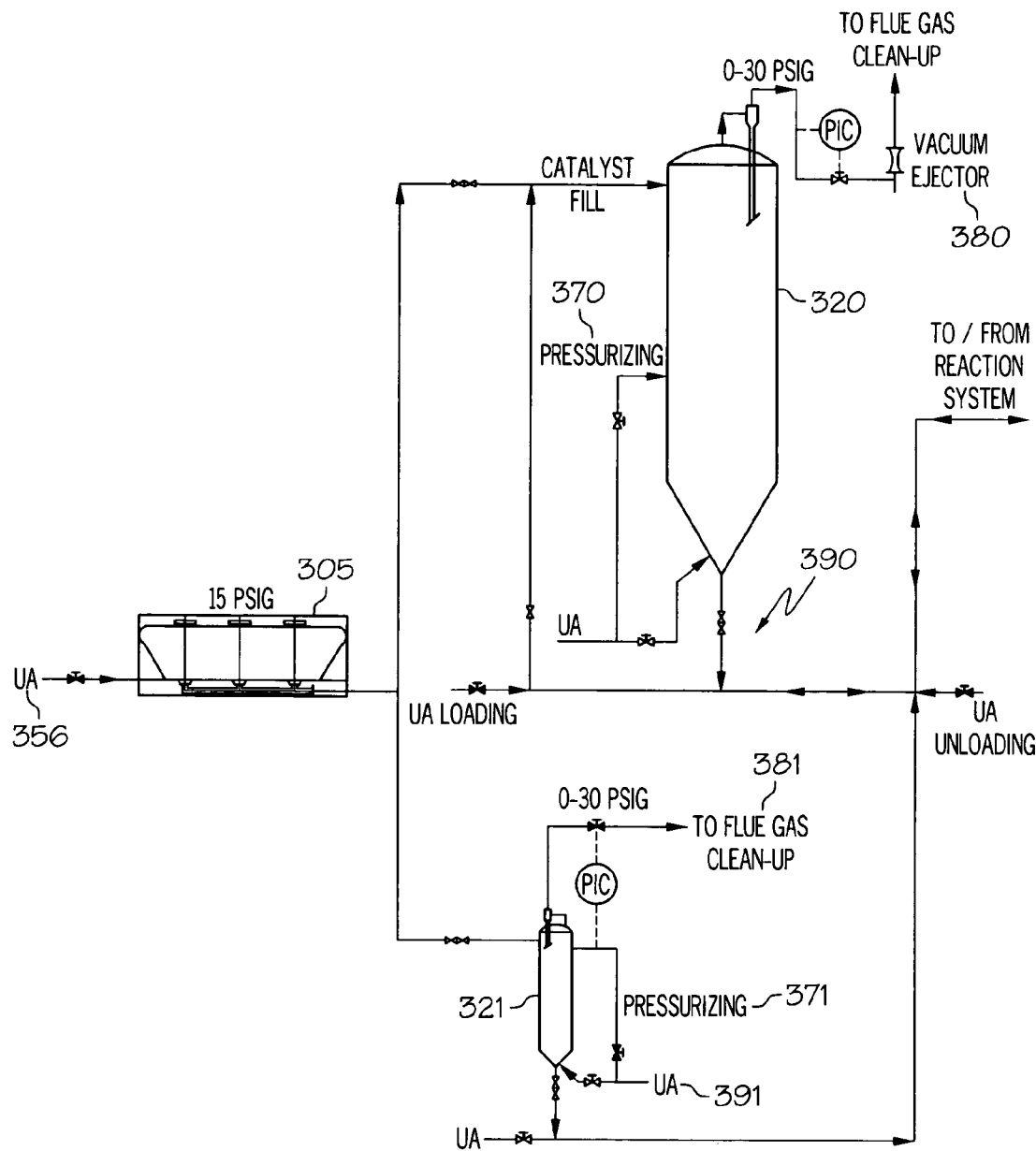
FIG. 3 is a schematic overview of a preferred embodiment of an entire catalyst handling system for transferring catalyst to a reaction system, and a system for unloading and reloading equilibrium catalyst from storage.

FIG. 3 schematically shows a preferred embodiment of a system for transferring catalyst particles from a transport or storage container into a reaction system. The catalyst particles are brought to the reaction system in one or more metal, pressurized storage containers 305. During transfer, a gas flow is introduced into the container 305. The gas flow assists the particles in flowing out of the storage container or feeder hopper. After the particles exit the storage container or feeder, the particles are propelled by a second gas flow from gas source 356 toward a vessel in the reaction system. In FIG. 3, the catalyst particles are being transferred into an intermediate hopper 320 or 321. The catalyst is then transferred generally at higher pressures from the intermediate hopper directly into a processing chamber in the reaction system, such as a reactor (not shown) or regenerator. The intermediate hopper 320 or 321 is equipped with a pressurizing system 370 or 371 to control the pressure within the intermediate hopper. The intermediate hopper also includes a release conduit 380 or 381 to exhaust any gas displaced when catalyst particles are added to the intermediate hopper and to control the intermediate hopper pressure. The intermediate hopper further includes an exit conduit 390 or 391. The exit conduit allows catalyst particles in the intermediate hopper to be transferred to other parts of the reaction system, such as the reactor or regenerator.

Figure 5:
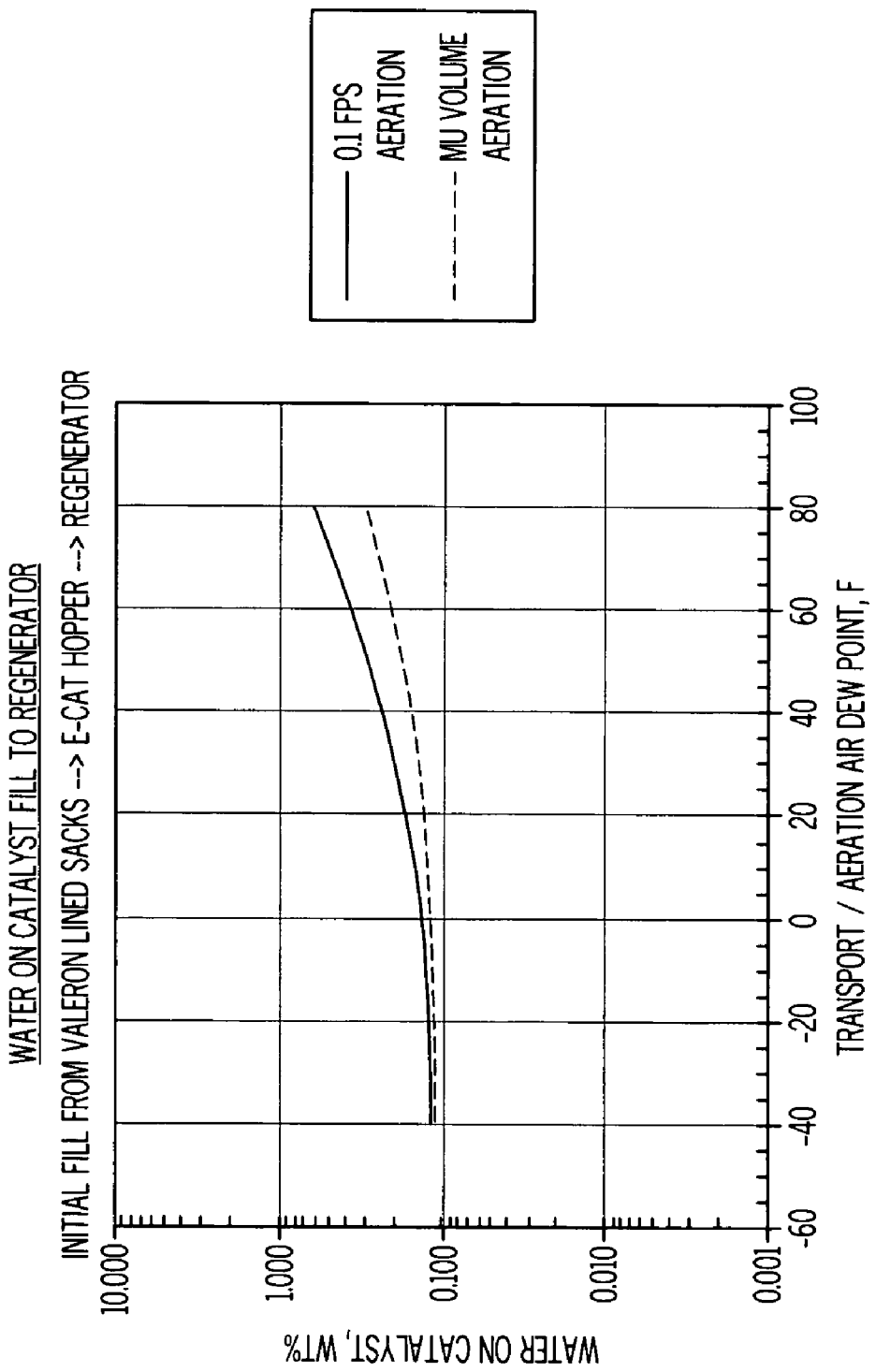
FIG. 5 is a plot of the potential incremental water uptake versus the atmospheric pressure dew point of the supplied aeration and transport gas for initial fresh catalyst delivered from Valeron lined sacks to an intermediate storage hopper and then to the reaction system and regenerator.

FIGS. 5-8 show calculated water uptake values for catalyst particles exposed to various embodiments of transfer processes according to the invention and as comparative examples. FIG. 5 shows water uptake for catalyst particles transferred from polymer lined (Valeron) sacks into a regenerator via an e-cat or other intermediate hopper. The two data lines show the water content of the catalyst particles transferred using a fixed flow of fluidization gas (0.1 fps) and catalyst particles transferred according to the invention, which uses a gas flow comparable in amount to the volume of catalyst and gas exiting the container. Due to the water permeable nature of the polymer lined sack, the catalyst particles show a minimum level of water content independent of the transfer process. However, the transfer process according to the invention still demonstrates an improvement over the water content of the process in the comparative example.

Figure 6:
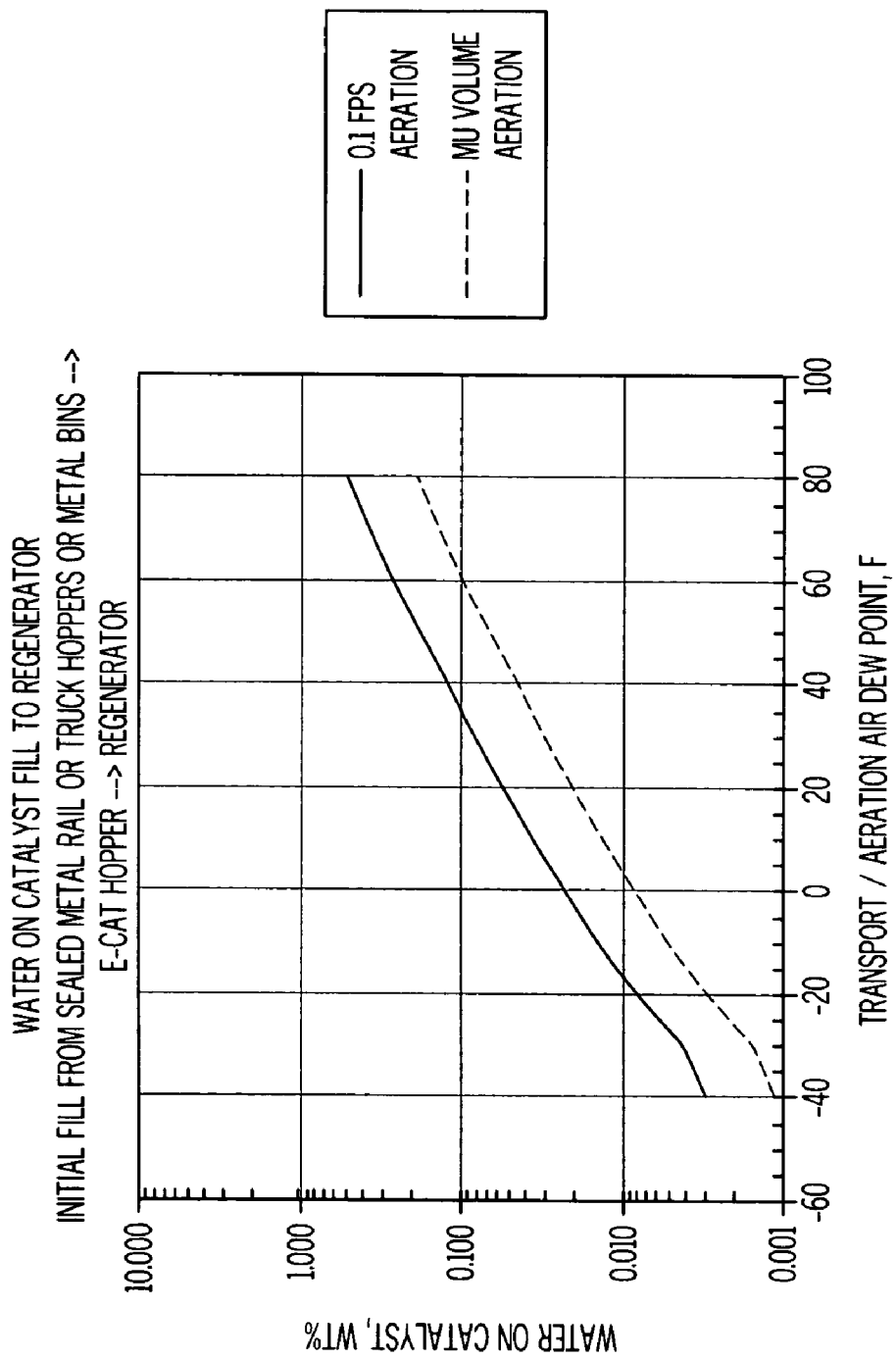
FIG. 6 is a plot of the potential incremental water uptake versus the atmospheric pressure dew point of the supplied aeration and transport gas for initial fresh catalyst delivered from a sealed metal container such as a sealed truck or rail hopper or sealed metal bin to an intermediate storage hopper and then to the reaction system and regenerator.

FIG. 6 shows water uptake for catalyst particles transferred from a pressurized metal container into a regenerator via an e-cat or other intermediate hopper. The two data lines show the difference in water content for catalyst particles transferred according to the claimed invention (lower data line) and a comparative example (upper data line). Because the pressurized metal container is not permeable to water, the catalyst particles can potentially have a lower water content. As a result, the catalyst particles are more sensitive to differences present in the transfer process. This increased sensitivity can be seen in FIG. 6, where the transfer process of the claimed invention leads to reduced water content on catalyst particles as compared with the comparative example.

Figure 7:
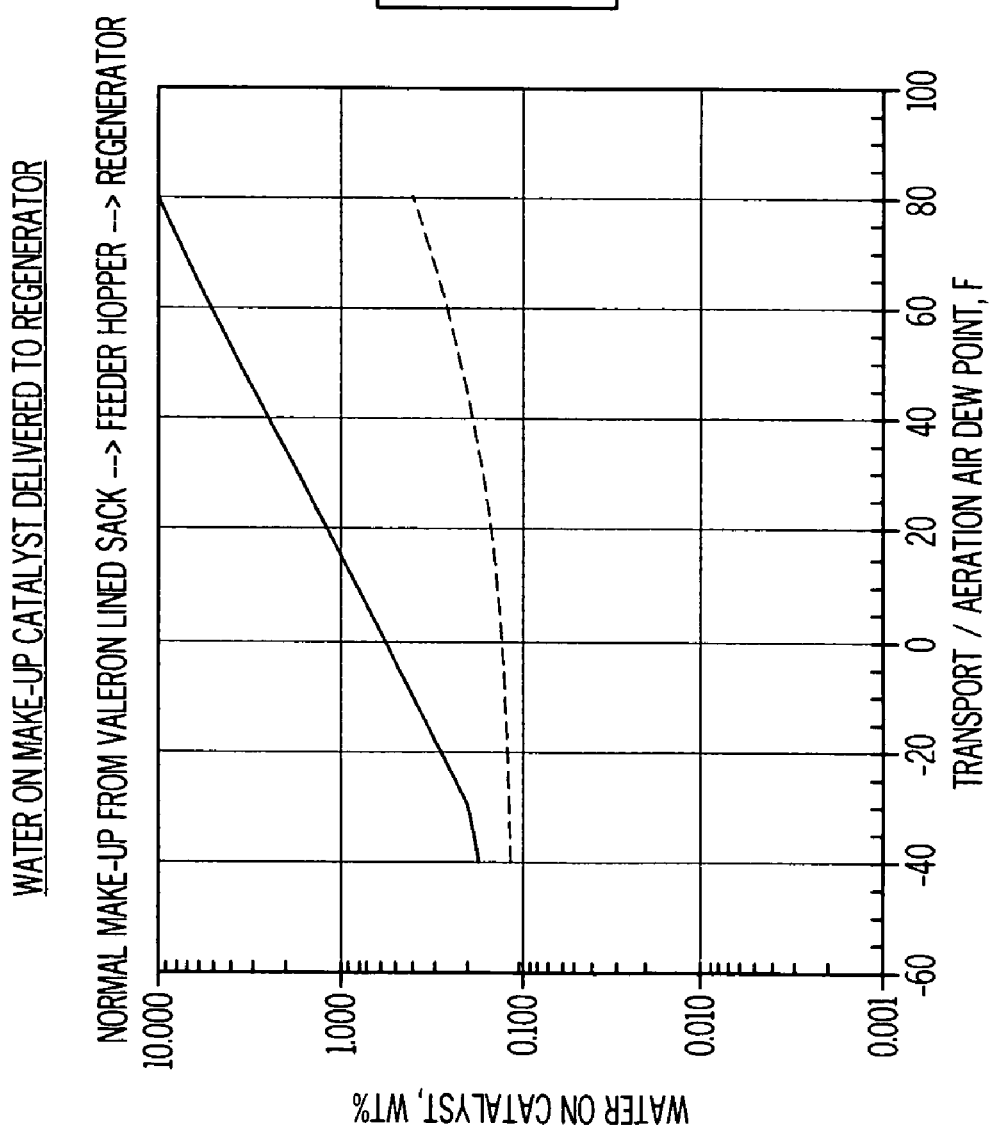
FIG. 7 is a plot of the potential incremental water uptake versus the atmospheric pressure dew point of the supplied aeration and transport gas for normal fresh catalyst delivered from Valeron lined sacks to another type of intermediate storage or feeder hopper and then to the reaction system and regenerator.
Figure 8:
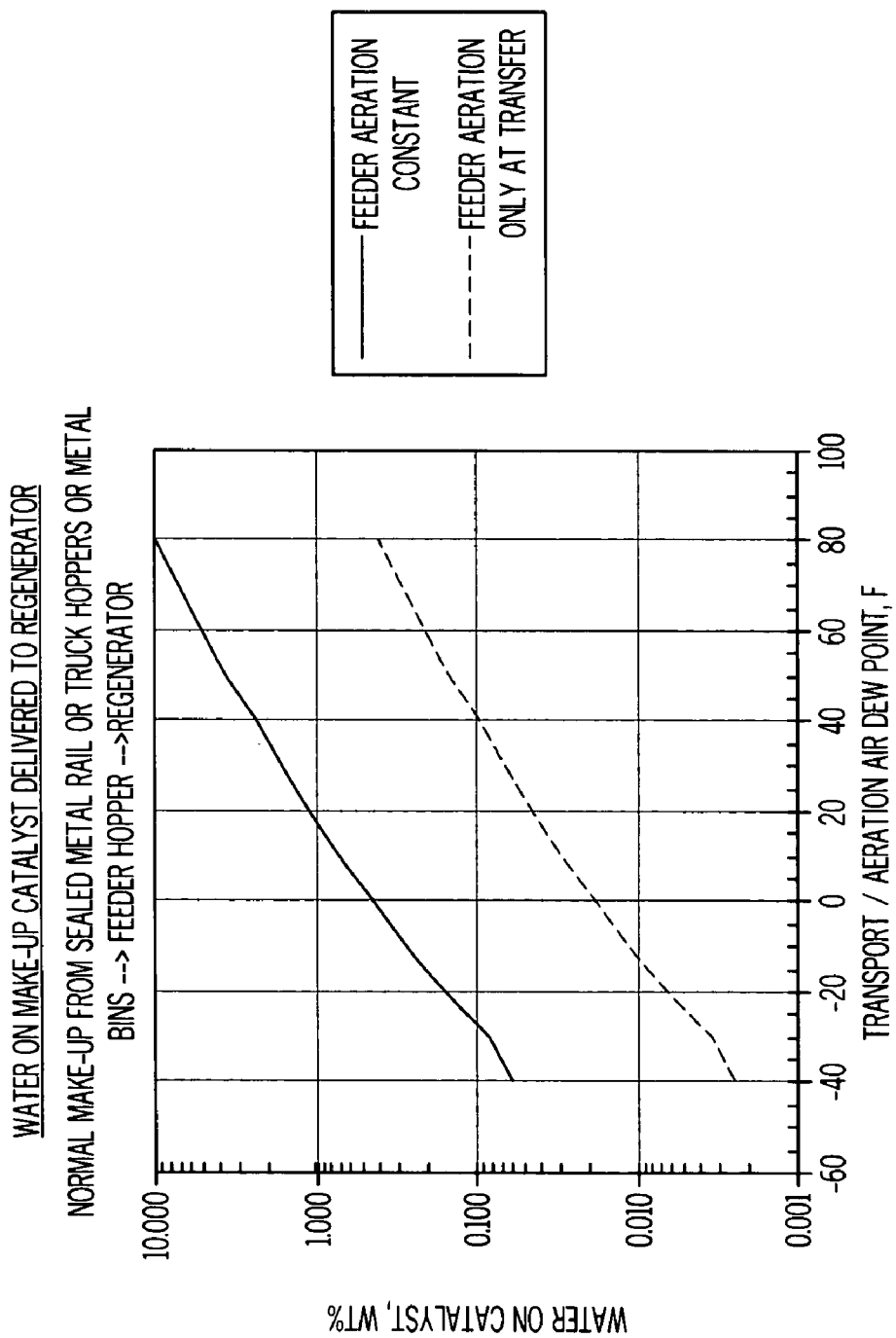
FIG. 8 is a plot of the potential incremental water uptake versus the atmospheric pressure dew point of the supplied aeration and transport gas for normal fresh catalyst delivered from a sealed metal container such as a sealed truck or rail hopper or sealed metal bin to another type of intermediate storage or feeder hopper and then to the reaction system and regenerator.

FIGS. 7 and 8 show water uptake for catalyst particles that are maintained in an intermediate hopper during the course of being transferred from a storage container to a reaction system such as a regenerator. FIG. 7 once again shows the water uptake for catalyst particles that were initially stored in polymer lined sacks prior to being maintained in the intermediate hopper. The two data lines represent transfer processes that either include a constant aeration flow for the intermediate hopper, or an aeration flow only during transfer operations according to the claimed invention. As before, the permeability of the polymer lined sacks results in a baseline level of water being present on the particles.

FIG. 8 shows the water uptake for catalyst particles that are stored in pressurized metal containers prior to being maintained in an intermediate hopper. As in FIG. 7, the lower data line corresponds to catalyst particles transferred according to the claimed invention, where the particles maintained in the intermediate hopper are only exposed to an aeration flow during catalyst particle transfer. The upper data line corresponds to catalyst particles subjected to a constant aeration flow prior to transfer.

VI. Molecular Sieve Activity

One method for measuring deactivation of the molecular sieve in this invention is by determining a catalytic activity index (CAI). The CAI provides a measure of catalyst deactivation as a result of catalyst exposure temperature, relative water pressure, and water contact time working in concert to deactivate the catalyst. Thus, for example, although a low relative water pressure generally causes less catalyst deactivation, higher relative water pressures may be mitigated by limiting the contact time or controlling the catalyst exposure temperature. The CAI formula of this invention fully describes allowable combinations of time, temperature and relative water pressure to limit catalyst deactivation to specified values.

The catalytic activity index of this invention is defined as the actual catalytic activity at time of measurement divided by the maximum catalytic activity (before any deactivation occurs). In this regard, the CAI would be 0 for a completely deactivated catalyst, and 1 for a catalyst having maximum catalytic activity.

The catalytic activity index (CAI) is calculated according to the following equation.

$$CAI = \exp(f(T) * f(PP_{water})^n * \mathrm{alpha} * t)$$

wherein t=time of contact of catalyst with water (hours)

T=temperature at contact (° C.)

$PP_{water}$=Partial Pressure of water in contact gas (psia)

alpha=−0.071 n=3.5

$f(T) = \exp(ea(1/(T+273) - 1/(T_o+273)))$ ea=−5500° K.

$T_o$=200° C.

$f(PP_{water}) = (26.2 * PP_{water}/P_{sat} + 1.14) * 0.175$, for T≧180° C. (453° K.)

$f(PP_{water}) = ((26.2 + 0.272*(180-T)) * PP_{water}/P_{sat} + 1.14) * 0.175$, for 180° C. (453° K.)>T≧150° C. (433° K)

$P_{sat}$=Saturation pressure of water at T (psia).

Preferably, any gas flows used to transfer catalyst particles into and from a reaction system are injected under conditions that do not significantly deactivate the catalyst. Preferably, the one or more gas flows are injected into the system, and the catalyst is maintained in the system, at conditions effective to maintain a catalytic activity index (CAI) at a predetermined level, where the catalyst is catalytically effective to convert feed to desired end product. Preferably the one or more gas flows are injected into the system and the catalyst is maintained in the reaction system at conditions effective to maintain a catalytic activity index of at least 0.7. More preferably, the gas flows are injected into the system and the catalyst is maintained in the reaction system at conditions effective to maintain a catalytic activity index of at least 0.8, and most preferably a catalytic activity index of at least 0.9.

Adsorption of water by activated molecular sieve can occur in situations where the catalyst is contained in the system at a temperature lower than water critical temperature and the system contains at least a measurable amount of water, i.e., a condition in which the system is not considered completely dry. In order to calculate the Catalytic Activity Index for catalyst particles, the moisture content of the gas the catalyst particles are exposed to can be expressed as a relative water pressure rather than as a dew point.

Relative water pressure ($P_r$) in this invention is defined as actual partial pressure of the water ($PP_{water}$) divided by saturated water pressure ($P_{sat}$) at a given temperature below the critical temperature of water. The relative water pressure is a measure of the wetness of the environment in which the activated molecular sieve is contacted with the gas. For example, a $P_r=1$ means 100% water saturation, and a $P_r=0$ means that the gas or environment is completely dry.

In this invention, relative water pressure of the reaction system or the transfer gas flow, or any other gas in the system, can range from very low, i.e., low humidity conditions, to a value of 1, saturated water conditions. For example, at 205° C., if the activated catalyst is contacted with room air (at 23° C. and at 71% relative humidity), this air contains water at a partial pressure of 0.29 psia (71/100*0.41=0.29, where 0.41 psia is the saturation water pressure at 23° C.). When this air is heated up to 205° C., the relative water pressure becomes 0.29/250=0.00116, where 250 psia is the saturation water pressure at 205° C. The relative humidity of the gas at 205° C. is 0.00116*100=0.116%. This example illustrates that one can use high humidity room air as a heating medium at elevated temperature to provide an environment having a low relative water pressure.

In general, the higher the water pressure, the greater the tendency of the activated catalyst to adsorb water, given constant catalyst exposure temperature and time of gas contact. The greater the amount of water adsorbed, the higher the rate of catalyst deactivation. Nevertheless, by increasing temperature or lowering time of contact, increased water pressure can be tolerated. It is preferred, however, that gas flows in the system be at an appropriate temperature or sufficiently dry so as to minimize adsorption of water by the activated catalyst.

In one embodiment, one or more gas flows are injected into the reaction system, or the gas in the reaction system is maintained, at a relative water pressure of not greater than 0.1. In another embodiment, the feed replacement gas is injected into the reaction system, or the gas in the reaction system is maintained, at a relative water pressure of not greater than 0.01; in another, a relative water pressure of not greater than 0.001, and in yet another a relative water pressure of not greater than 0.0001.

VII. Type of Reaction Systems Encompassed by the Invention

The transfer methods of this invention are useful in any reaction system that involves the use of catalyst that comprises any molecular sieve material susceptible to loss of catalytic activity due to contact with water molecules. Non-limiting examples of such reaction systems include reaction systems selected from the group consisting of catalytic cracking reaction systems, transalkylation reaction systems, isomerization reaction systems, catalytic dewaxing systems, alkylation reaction systems, hydrocracking reaction systems, systems for converting paraffins to olefins, systems for converting paraffins to aromatics, systems for converting olefins to gasoline, systems for converting olefins to distillate, systems for converting olefins to lubes, systems for converting alcohols to olefins, disproportionation reaction systems, systems for converting aromatics to higher aromatics, systems for adsorbing aromatics, systems for converting oxygenates (e.g., alcohols) to olefins, systems for converting oxygenates (e.g., alcohols) to aromatics, systems for oligomerizing olefins, and systems for converting unsaturated hydrocarbons to aldehydes. More specifically, such examples include:

A) The catalytic cracking of a naphtha feed to produce light olefins. Typical reaction conditions include from about 500° C. to about 750° C., pressures of subatmospheric or atmospheric, generally ranging up to about 10 atmospheres (gauge) and residence time (time of contact of feed and/or product with catalyst) from about 10 milliseconds to about 10 seconds;

B) The catalytic cracking of high molecular weight hydrocarbons to lower weight hydrocarbons. Typical reaction conditions for catalytic cracking include temperatures of from about 400° C. to about 700° C., pressures of from about 0.1 atmosphere (bar) to about 30 atmospheres, and weight hourly space velocities of from about 0.1 $hr^{-1}$ to about 100 $hr^{-1}$;

C) The transalkylation of aromatic hydrocarbons in the presence of polyalkylaromatic hydrocarbons. Typical reaction conditions include a temperature of from about 200° C. to about 500° C., a pressure of from about atmospheric to about 200 atmospheres, a weight hourly space velocity of from about 1 $hr^{-1}$ to about 100 $hr^{-1}$, and an aromatic hydrocarbon/polyalkylaromatic hydrocarbon mole ratio of from about 1/1 to about 16/1;

D) The isomerization of aromatic (e.g., xylene) feedstock components. Typical reaction conditions for such include a temperature of from about 230° C. to about 510° C., a pressure of from about 0.5 atmospheres to about 50 atmospheres, a weight hourly space velocity of from about 0.1 $hr^{-1}$ to about 200 $hr^{-1}$, and a hydrogen/hydrocarbon mole ratio of from about 0 to about 100/1;

E) The catalytic dewaxing of hydrocarbons by selectively removing straight chain paraffins. The reaction conditions are dependent in large measure on the feed used and upon the desired pour point. Typical reaction conditions include a temperature between about 200° C. and 450° C., a pressure of up to 3,000 psig and a liquid hourly space velocity from 0.1 $hr^{-1}$ to 20 $hr^{-1}$.

F) The alkylation of aromatic hydrocarbons, e.g., benzene and alkylbenzenes, in the presence of an alkylating agent, e.g., olefins, formaldehyde, alkyl halides and alcohols having 1 to about 20 carbon atoms. Typical reaction conditions include a temperature of from about 100° C. to about 500° C., a pressure of from about atmospheric to about 200 atmospheres, a weight hourly space velocity of from about 1 $hr^{-1}$ to about 100 $hr^{-1}$, and an aromatic hydrocarbon/alkylating agent mole ratio of from about 1/1 to about 20/1;

G) The alkylation of aromatic hydrocarbons, e.g., benzene, with long chain olefins, e.g., $C_{14}$ olefin. Typical reaction conditions include a temperature of from about 50° C. to about 200° C., a pressure of from about atmospheric to about 200 atmospheres, a weight hourly space velocity of from about 2 $hr^{-1}$ to about 2000 $hr^{-1}$, and an aromatic hydrocarbon/olefin mole ratio of from about 1/1 to about 20/1. The resulting products from the reaction are long chain alkyl aromatics, which when subsequently sulfonated have particular application as synthetic detergents;

H) The alkylation of aromatic hydrocarbons with light olefins to provide short chain alkyl aromatic compounds, e.g., the alkylation of benzene with propylene to provide cumene. Typical reaction conditions include a temperature of from about 10° C. to about 200° C., a pressure of from about 1 to about 30 atmospheres, and an aromatic hydrocarbon weight hourly space velocity (WHSV) of from 1 $hr^{-1}$ to about 50 $hr^{-1}$;

I) The hydrocracking of heavy petroleum feedstocks, cyclic stocks, and other hydrocrack charge stocks. The catalyst will contain an effective amount of at least one hydrogenation component;

J) The alkylation of a reformate containing substantial quantities of benzene and toluene with fuel gas containing short chain olefins (e.g., ethylene and propylene) to produce mono- and dialkylates. Preferred reaction conditions include temperatures from about 100° C. to about 250° C., a pressure of from about 100 psig to about 800 psig, a WHSV-olefin from about 0.4 $hr^{-1}$ to about 0.8 $hr^{-1}$, a WHSV-reformate of from about 1 $hr^{-1}$ to about 2 $hr^{-1}$ and, optionally, a gas recycle from about 1.5 to about 2.5 vol/vol fuel gas feed;

K) The alkylation of aromatic hydrocarbons, e.g., benzene, toluene, xylene, and naphthalene, with long chain olefins, e.g., $C_{14}$ olefin, to produce alkylated aromatic lube base stocks. Typical reaction conditions include temperatures from about 100° C. to about 400° C. and pressures from about 50 psig to 450 psig;

L) The alkylation of phenols with olefins or equivalent alcohols to provide long chain alkyl phenols. Typical reaction conditions include temperatures from about 100° C. to about 250° C., pressures from about 1 to 300 psig and total WHSV of from about 2 $hr^{-1}$ to about 10 $hr^{-1}$;

M) The conversion of light paraffins to olefins and/or aromatics. Typical reaction conditions include temperatures from about 425° C. to about 760° C. and pressures from about 10 psig to about 2000 psig;

N) The conversion of light olefins to gasoline, distillate and lube range hydrocarbons. Typical reaction conditions include temperatures of from about 175° C. to about 375° C., and a pressure of from about 100 psig to about 2000 psig;

O) Two-stage hydrocracking for upgrading hydrocarbon streams having initial boiling points above about 200° C. to premium distillate and gasoline boiling range products or as feed to further fuels or chemicals processing steps. Either stage of the two-stage system can contain catalyst, which contains molecular sieve that is susceptible to loss of catalytic activity due to contact with water molecules. Typical reaction conditions include temperatures of from about 315° C. to about 455° C., pressures of from about 400 to about 2500 psig, hydrogen circulation of from about 1000 SCF/bbl to about 10,000 SCF/bbl and a liquid hourly space velocity (LHSV) of from about 0.1 $hr^{-1}$ to 10 $hr^{-1}$;

P) A combination hydrocracking/dewaxing process in the presence of a catalyst that contains molecular sieve that is susceptible to loss of catalytic activity due to contact with water molecules. The catalyst generally further comprises a hydrogenation component. Optionally included in the catalyst is zeolite molecular sieve such as zeolite Beta. Typical reaction conditions include temperatures from about 350° C. to about 400° C., pressures from about 1400 psig to about 1500 psig, LHSVs from about 0.4 $hr^{-1}$ to about 0.6 $hr^{-1}$ and a hydrogen circulation from about 3000 to about 5000 SCF/bbl;

Q) The reaction of alcohols with olefins to provide mixed ethers, e.g., the reaction of methanol with isobutene and/or isopentene to provide methyl-t-butyl ether (MTBE) and/or t-amyl methyl ether (TAME). Typical conversion conditions include temperatures from about 20° C. to about 200° C., pressures from 2 to about 200 atm, WHSV (gram-olefin per hour gram-zeolite) from about 0.1 $hr^{-1}$ to about 200 $hr^{-1}$ and an alcohol to olefin molar feed ratio from about 0.1/1 to about 5/1;

R) The disproportionation of aromatics, e.g., the disproportionation toluene to make benzene and paraxylene. Typical reaction conditions include a temperature of from about 200° C. to about 760° C., a pressure of from about atmospheric to about 60 atmosphere (bar), and a WHSV of from about 0.1 $hr^{-1}$ to about 30 $hr^{-1}$;

S) The conversion of naphtha (e.g., $C_6$-$C_{10}$) and similar mixtures to highly aromatic mixtures. Thus, normal and slightly branched chained hydrocarbons, preferably having a boiling range above about 40° C., and less than about 200° C., can be converted to products having a substantially higher octane aromatics content by contacting the hydrocarbon feed with a molecular sieve catalyst at a temperature of from about 400° C. to 600° C., preferably from about 480° C. to about 550° C., at pressures of from atmospheric to 40 bar, and liquid hourly space velocities (LHSV) of from 0.1 $hr^{-1}$ to 15 $hr^{-1}$;

T) The adsorption of alkyl aromatic compounds for the purpose of separating various isomers of the compounds;

U) The conversion of oxygenates, e.g., alcohols, such as methanol, or ethers, such as dimethylether, or mixtures thereof to hydrocarbons including olefins and aromatics with reaction conditions including temperatures of from about 275° C. to about 600° C., pressures of from about 0.5 atmosphere to about 50 atmospheres, and a liquid hourly space velocity of from about 0.1 $hr^{-1}$ to about 100 $hr^{-1}$;

V) The oligomerization of straight and branched chain olefins having from about 2 to about 5 carbon atoms. The oligomers which are the products of the process are medium to heavy olefins which are useful for both fuels, i.e., gasoline or a gasoline blending stock, and chemicals. The oligomerization process is generally carried out by contacting the olefin feedstock in a gaseous state phase with a molecular sieve catalyst at a temperature in the range of from about 250° C. to about 800° C., a LHSV of from about 0.2 $hr^{-1}$ to about 50 $hr^{-1}$, and a hydrocarbon partial pressure of from about 0.1 to about 50 atmospheres. Temperatures below about 250° C. may be used to oligomerize the feedstock when the feedstock is in the liquid phase when contacting the coated zeolite catalyst. Thus, when the olefin feedstock contacts the catalyst in the liquid phase, temperatures of from about 10° C. to about 250° C. may be used;

W) The conversion of $C_2$ unsaturated hydrocarbons (ethylene and/or acetylene) to aliphatic $C_{6-12}$ aldehydes and converting said aldehydes to the corresponding $C_{6-12}$ alcohols, acids, or esters.

In general, the, catalytic conversion conditions over the molecular sieve catalyst include a temperature of from about 100° C. to about 760° C., a pressure of from about 0.1 atmosphere (bar) to about 200 atmospheres (bar), a weight hourly space velocity of from about 0.08 $hr^{-1}$ to about 2,000 $hr^{-1}$.

The catalyst transfer methods of this invention are particularly suited to large, commercial scale reaction systems. For example, the transfer methods of this invention are particularly suited to reaction systems that require a catalyst loading of at least about 1,000 kg of catalyst, based on total amount of catalyst located throughout the reaction system. In particular, the transfer methods of this invention are particularly suited to reaction systems that require a catalyst loading of at least about 10,000 kg of catalyst, more particularly a catalyst loading of at least about 100,000 kg of catalyst, and most particularly a catalyst loading of at least about 250,000 kg of catalyst, based on total amount of catalyst located throughout the reaction system.

The catalyst that is used in the reaction system need not be fully comprised of a molecular sieve that is susceptible to loss of catalytic activity due to contact with water molecules. The catalyst need contain only an amount of such molecular sieve that materially affects the desired product slate. For example, in one embodiment, the catalyst used in the system comprises at least about 1 wt % of a molecular sieve that is susceptible to loss of catalytic activity due to contact with water molecules, based on total weight of catalyst in the system. In anther embodiment, the catalyst used in the system comprises at least about 5 wt % of a molecular sieve that is susceptible to loss of catalytic activity due to contact with water molecules, based on total weight of catalyst in the system; in another embodiment at least about 10 wt %, based on total weight of catalyst in the system.

The liquid feed that is flowed to the reaction system in operation is any conventional hydrocarbon feed that is appropriate to the particular unit. Non-limiting examples of such feed includes hydrocarbon oils such as kerosenes, naphthas, diesels, light or heavy gas oils, vacuum distillates or residua, light cycle oils, heavy cycle oils; aromatics such as benzenes, xylenes, toluenes, naphthalenes; and alcohols, including monoalcohols or polyols, particularly $C_1$-$C_{10}$ monoalcohols (especially methanol, ethanol and propanol) and $C_3$-$C_{10}$ polyols.

The catalyst used in the system can be of any conventional shape or size, including, but not limited to, those catalyst types made by spray drying, pelletizing, extrusion, and any of various conventional sphere-making techniques. The molecular sieve contained in the catalyst can be incorporated into each catalyst particle or catalyst particles containing the molecular sieve can be admixed with other catalyst particles that do not contain molecular sieve.

The reaction systems that incorporate the processes of this invention contain a reactor unit. Optionally, the reaction systems contain two or more reactor units. The reactor units can be in series or parallel. Non-limiting examples of reaction systems which can be shut down according to this invention include dense bed reaction systems, fixed bed reaction systems, fluidized bed reaction systems, fast fluidized bed reaction systems, circulating fluidized bed reaction systems, riser reactor systems, and the like. Suitable conventional reaction systems and reactor types are described in for example U.S. Pat. No. 4,076,796, U.S. Pat. No. 6,287, 522 (dual riser), and *Fluidization Engineering,* D. Kunii and O. Levenspiel, Robert E. Krieger Publishing Company, New York, N.Y. 1977, which are all herein fully incorporated by reference. Other examples of reaction systems include riser reactors, such as those generally described in *Riser Reactor, Fluidization and Fluid-Particle Systems,* pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564, 613 filed May 4, 2000 (multiple riser reactor), which references are all herein fully incorporated by reference.

In a preferred embodiment, the reaction system is a fluidized bed process or fast fluidized bed process, and the process includes a reactor system, a regeneration system and a recovery system. The reactor system preferably is a fluid bed reactor system, and includes a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock is fed to the one or more riser reactor(s) in which an activated molecular sieve catalyst composition is introduced.

In another embodiment, the catalyst transfer processes of this invention are particularly directed to reaction systems that further include a regenerator unit. Optionally, the reaction systems include two or more regenerator units. The regenerator units are in connection with at least one of the reactor units, preferably in a manner that allows catalyst to be circulated or flowed between the reactor and regenerator.

VIII. Types of Catalyst

The catalyst that is used in the methods of this invention contains molecular sieve material that is susceptible to deactivation due to contact with water molecules. The molecular sieves that are included in the catalyst or catalyst mixtures are preferably aluminophosphate and/or metalloaluminophosphate molecular sieves that have a molecular framework that include [AlO4] and [PO4] tetrahedral units, such as metal containing aluminophosphates (AlPO). In one embodiment, the metalloaluminophosphate molecular sieves include [AlO4], [PO4] and [SiO4] tetrahedral units, such as silicoaluminophosphates (SAPO). In alternative embodiments, the methods of this invention can also generally be used with other molecular sieve materials that can be deactivated by exposure to water vapor to a catalytic activity index of 0.7 or less, or 0.8 or less, or 0.9 or less.

Various silicon, aluminum, and phosphorus based molecular sieves and metal-containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO4), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500, 651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference. Other molecular sieves include those described in R. Szostak, Handbook of Molecular Sieves, Van Nostrand Reinhold, New York, N.Y. (1992), which is herein fully incorporated by reference.

The more preferred molecular sieves are SAPO molecular sieves, and metal-substituted SAPO molecular sieves. Suitable metal substituents are alkali metals of Group IA of the Periodic Table of Elements, an alkaline earth metals of Group IIA of the Periodic Table of Elements, a rare earth metals of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, transition metals of Groups IVB, VB, VIB, VIIB, VIIIB, and IB of the Periodic Table of Elements and mixtures of any of these metal species. In one embodiment, the metal is selected from the group consisting of Co, Cr, Cu, Fe, Ga, Ge, Mg, Mn, Ni, Sn, Ti, Zn and Zr, and mixtures thereof. The metal atoms may be inserted into the framework of a molecular sieve through a tetrahedral unit, such as [MeO2], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the metalloaluminophosphate molecular sieve is represented, on an anhydrous basis, by the formula:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from the group consisting of Group IA, IIA, IB, IIIB, IVB, VB, VIB, VIIB, VIIIB and Lanthanide's of the Periodic Table of Elements. Preferably M is one or more metals selected from the group consisting of Si, Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

In one embodiment of the invention, the metalloaluminophosphate molecular sieves contain silicon and aluminum. In general, lower Si/Al ratios lead to lower deactivation rates and higher ACIs for a given set of conditions. However, higher Si/Al ratios can be used under the appropriate conditions of temperature, water partial pressure and time of contact with water. Desirably, the metalloaluminophosphate molecular sieves of this invention contain Si and Al, at a Si/Al ratio of not greater than about 0.5, preferably not greater than about 0.3, more preferably not greater than about 0.2, still more preferably not greater than about 0.15, and most preferably not greater than about 0.1. In another embodiment, the Si/Al ratio is sufficiently high to allow for increased catalytic activity of the molecular sieve. Preferably, the metalloaluminophosphate molecular sieves contain Si and Al at a ratio of at least about 0.005, more preferably at least about 0.01, and most preferably at least about 0.02.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO-18, AlPO-34 and metal containing derivatives thereof, such as one or a combination of SAPO-18, SAPO-34, AlPO-34, AlPO-18, and metal containing derivatives thereof, and especially one or a combination of SAPO-34, AlPO-18, and metal containing derivatives thereof.

In an embodiment, the molecular sieve is an intergrowth material having two or more distinct crystalline phases within one molecular sieve composition. In particular, intergrowth molecular sieves are described in U.S. Patent Application Publication No. 2002-0165089 and International Publication No. WO 98/15496, published Apr. 16, 1998, both of which are herein fully incorporated by reference. For example, SAPO-18, AlPO-18 and RUW-18 have an AEI framework-type, and SAPO-34 has a CHA framework-type. Thus, the molecular sieve used herein may comprise at least one intergrowth phase of AEI and CHA framework-types, especially where the ratio of CHA framework-type to AEI framework-type, as determined by the DIFFaX method disclosed in U.S. Patent Application Publication No. 2002-0165089, is greater than 1:1.

Generally, molecular sieves (i.e., molecular sieve crystals) are synthesized by the hydrothermal crystallization of one or more of a source of aluminum, a source of phosphorus, a source of silicon, water and a templating agent, such as a nitrogen containing organic compound. Typically, a combination of sources of silicon and aluminum, or silicon, aluminum and phosphorus, water and one or more templating agents, is placed in a sealed pressure vessel. The vessel is optionally lined with an inert plastic such as polytetrafluoroethylene, and heated under a crystallization pressure and temperature, until a crystalline material is formed, which can then be recovered by filtration, centrifugation and/or decanting.

In general, templating agents or templates include compounds that contain elements of Group 15 of the Periodic Table of Elements, particularly nitrogen, phosphorus, arsenic and antimony. Typical templates also contain at least one alkyl or aryl group, such as an alkyl or aryl group having from 1 to 10 carbon atoms, for example from 1 to 8 carbon atoms. Preferred templates are nitrogen-containing compounds, such as amines, quaternary ammonium compounds and combinations thereof. Suitable quaternary ammonium compounds are represented by the general formula $R_4N^+$, where each R is hydrogen or a hydrocarbyl or substituted hydrocarbyl group, preferably an alkyl group or an aryl group having from 1 to 10 carbon atoms.

Once the crystalline molecular sieve product is formed, usually in a slurry state, it may be recovered by any standard technique well known in the art, for example, by centrifugation or filtration. The recovered crystalline particle product, normally termed the "wet filter cake", may then be washed, such as with water, and then dried, such as in air, before being formulated into a catalyst composition. Alternatively, the wet filter cake may be formulated into a catalyst composition directly, that is without any drying, or after only partial drying.

In one embodiment, the molecular sieve that is susceptible to deactivation due to contact with water molecules is contained in a formulated catalyst. In general, formulated molecular sieve catalyst optionally contains binder and matrix materials. Conventionally, formulated catalyst is made by mixing together molecular sieve crystals (which includes template) and a liquid, optionally with matrix material and/or binder, to form a slurry. The slurry is then dried (i.e., liquid is removed), without completely removing the template from the molecular sieve. Since this dried molecular sieve catalyst includes template, it has not been activated, and is considered a preformed catalyst. The catalyst in this form is resistant to catalytic loss by contact with moisture or water. However, the preformed catalyst must be activated before use and this invention provides appropriate methods to protect the activated catalyst from significant deactivation.

The liquid used to form the slurry can be any liquid conventionally used in formulating molecular sieve catalysts. Non-limiting examples of suitable liquids include water, alcohol, ketones, aldehydes, esters, or a combination thereof. Water is a preferred liquid.

Matrix materials are optionally included in the slurry used to make the formulated molecular sieve catalyst of this invention. Such materials are typically effective as thermal sinks assisting in shielding heat from the catalyst composition, for example, during regeneration. They can further act to densify the catalyst composition, increase catalyst strength such as crush strength and attrition resistance, and to control the rate of conversion in a particular process. Non-limiting examples of matrix materials include one or more of: rare earth metals, metal oxides including titania, zirconia, magnesia, thoria, beryllia, quartz, silica or sols, and mixtures thereof; for example, silica-magnesia, silica-zirconia, silica-titania, silica-alumina and silica-alumina-thoria.

In one embodiment, matrix materials are natural clays, such as those from the families of montmorillonite and kaolin. These natural clays include kaolins known as, for example, Dixie, McNamee, Georgia and Florida clays. Non-limiting examples of other matrix materials include: halloysite, kaolinite, dickite, nacrite, or anauxite. Optionally, the matrix material, preferably any of the clays, are calcined, acid treated, and/or chemical treated before being used as a slurry component. Under the optional calcination treatment, the matrix material will still be considered virgin material as long as the material has not been previously used in a catalyst formulation.

In a particular embodiment, the matrix material is a clay or a clay-type composition, preferably a clay or clay-type composition having a low iron or titania content, and most preferably the matrix material is kaolin. Kaolin has been found to form a pumpable, high solid content slurry; it has a low fresh surface area, and it packs together easily due to its platelet structure.

Preferably, the matrix material, particularly clay, and preferably kaolin, has an average particle size of from about 0.05 μm to about 0.75 μm; more preferably from about 0.1 μm to about 0.6 μm. It is also desirable that the matrix material have a $d_{90}$ particle size distribution of less than about 1.5 μm, preferably less than about 1 μm.

Binders are also optionally included in the slurry used to make the formulated molecular sieve catalysts of this invention. Such materials act like glue, binding together the molecular sieve crystals and other materials, to form a formulated catalyst composition. Non-limiting examples of binders include various types of inorganic oxide sols such as hydrated aluminas, silicas, and/or other inorganic oxide sols. In one embodiment of the invention, the binder is an alumina-containing sol, preferably aluminium chlorohydrate. Upon calcining, the inorganic oxide sol, is converted into an inorganic oxide matrix component, which is particularly effective in forming a hardened molecular sieve catalyst composition. For example, an alumina sol will convert to an aluminium oxide matrix following heat treatment.

Aluminium chlorohydrate, a hydroxylated aluminium based sol containing a chloride counter ion, also known as aluminium chlorohydrol, has the general formula

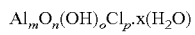
$Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., *Stud. Surf. Sci. and Catal.*, 76, pages 105-144, Elsevier, Amsterdam, 1993, which is herein incorporated by reference. In another embodiment, one or more binders are present in combination with one or more other non-limiting examples of alumina materials such as aluminium oxyhydroxide, γ-alumina, boehmite and transitional aluminas such as α-alumina, β-alumina, γ-alumina, δ-alumina, ε-alumina, κ-alumina, and ρ-alumina, aluminium trihydroxide, such as gibbsite, bayerite, nordstrandite, doyelite, and mixtures thereof.

In another embodiment, the binders are alumina sols, predominantly comprising aluminium oxide, optionally including silicon. In yet another embodiment, the binders are peptised alumina made by treating alumina hydrates such as pseudobohemite, with an acid, preferably a non-halogen acid, to prepare sols or aluminium ion solutions. Non-limiting examples of commercially available colloidal alumina sols include Nalco 8676 available from Nalco Chemical Co., Naperville, Ill., and Nyacol available from the Nyacol Nano Technology Inc., Boston, Mass.

If binder is not used in making the molecular sieve catalyst, the catalyst is considered a binderless catalyst. If binder is used, the amount of binder used to prepare the molecular sieve catalyst ranges from about 2% by weight to about 30% by weight, based on the total weight of the binder, the molecular sieve, and optionally included matrix material, excluding the liquid (i.e., after drying). Preferably the amount of binder used to prepare the molecular sieve catalyst ranges from about 5% by weight to about 20% by weight, more preferably from about 7% by weight to about 15% by weight, based on the total weight of the binder, the molecular sieve, and optionally included matrix material, excluding the liquid (i.e., after drying).

Where the catalyst composition contains a binder and a matrix material, the weight ratio of the binder to the matrix material is typically from 1:15 to 1:5, such as from 1:10 to 1:4, and particularly from 1:6 to 1:5. The amount of binder is typically from about 2% by weight to about 30% by weight, such as from about 5% by weight to about 20% by weight, and particularly from about 7% by weight to about 15% by weight, based on the total weight of the binder, the molecular sieve and matrix material. It has been found that a higher sieve content and lower matrix content increases the molecular sieve catalyst composition performance, whereas a lower sieve content and higher matrix content improves the attrition resistance of the composition.

In general, the amount of binder and/or matrix material is such that the formulated molecular sieve catalyst composition contains from about 1% to about 99%, such as from about 10% to about 90%, such as from about 10% to about 80%, for example from about 20% to about 70%, and conveniently from about 25% to about 60% by weight of the molecular sieve, based on the total weight of the formulated molecular sieve catalyst composition.

The molecular sieve material is activated by removing the template from the preformed molecular sieve catalyst composition so as to expose the active catalytic sites to the environment. The template can be removed by any conventional technique, including for example by elution methods or by heating. The molecular sieve crystals themselves can be activated for immediate catalytic use or for storing or transporting prior to use. However, it is preferred that the molecular sieves be formulated into a preformed catalyst, then activated, since the sieves are typically most useful as a formulated product. The formulated product generally provides the most effective particle size and hardness for commercial scale equipment.

In one embodiment of the invention, the molecular sieve material is activated by removing the template by heat. In a preferred embodiment, the heat is sufficient to remove water that is formed as a result of the combustion of the template. Preferably, the molecular sieve material is heated at a temperature greater than the critical temperature of water. At this temperature, water formed during the combustion process will not condense or be retained by the molecular sieve. Preferably, the template is removed by contacting with steam at a temperature greater than the critical temperature of water. More preferably, following removal of the template, any water entrained in the catalyst is also removed, preferably by appropriate heating using a dry gas. Preferably, the dry gas has a relative water pressure of less than 0.0001.

Heating to remove template and activate the molecular sieve is generally referred to in this invention as calcination. Conventional calcination devices can be used. Such devices include rotary calciners, fluid bed calciners, batch ovens, and the like. Calcination time is typically dependent on the degree of hardening of the molecular sieve catalyst composition and the temperature.

Conventional calcination temperatures are effective to remove template materials and to activate the molecular sieve catalyst of this invention. Such temperatures are generally in the range from about 400° C. to about 1,000° C., preferably from about 500° C. to about 800° C., and most preferably from about 550° C. to about 700° C.

IX. Detailed Description of Preferred Reaction Systems

In a preferred embodiment of the invention, the reaction system is a system for converting oxygenates to olefins or a catalytic cracking reaction system. More preferably, the reaction system is a system for converting oxygenates to olefins or an olefin forming reaction system. The reaction system preferably includes both a reactor and a regenerator.

In one embodiment of the invention, the reaction system is an olefin forming reaction system in which feedstock is converted into one or more olefin(s). Typically, the feedstock contains one or more aliphatic-containing compounds such that the aliphatic moiety contains from 1 to about 50 carbon atoms, such as from 1 to 20 carbon atoms, for example from 1 to 10 carbon atoms, and particularly from 1 to 4 carbon atoms.

Non-limiting examples of aliphatic-containing compounds include alcohols such as methanol and ethanol, alkyl mercaptans such as methyl mercaptan and ethyl mercaptan, alkyl sulfides such as methyl sulfide, alkylamines such as methylamine, alkyl ethers such as dimethyl ether, diethyl ether and methylethyl ether, alkyl halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene.

The catalyst composition of the invention is particularly useful in the process that is generally referred to as the gas-to-olefins (GTO) process or, alternatively, the methanol-to-olefins (MTO) process. In this process, an oxygenated feedstock, most preferably a methanol-containing feedstock, is converted in the presence of a molecular sieve catalyst composition into one or more olefin(s), preferably and predominantly, ethylene and/or propylene.

Using the catalyst composition of the invention for the conversion of a feedstock, preferably a feedstock containing one or more oxygenates, the amount of olefin(s) produced based on the total weight of hydrocarbon produced is greater than 50 weight percent, typically greater than 60 weight percent, such as greater than 70 weight percent, and preferably greater than 75 weight percent. In one embodiment, the amount of ethylene and/or propylene produced based on the total weight of hydrocarbon product produced is greater than 65 weight percent, such as greater than 70 weight percent, for example greater than 75 weight percent, and preferably greater than 78 weight percent. Typically, the amount ethylene produced in weight percent based on the total weight of hydrocarbon product produced, is greater than 30 weight percent, such as greater than 35 weight percent, for example greater than 40 weight percent. In addition, the amount of propylene produced in weight percent based on the total weight of hydrocarbon product produced is greater than 20 weight percent, such as greater than 25 weight percent, for example greater than 30 weight percent, and preferably greater than 35 weight percent.

In addition to the oxygenate component, such as methanol, the feedstock may contain one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition.

The present process can be conducted over a wide range of temperatures, such as in the range of from about 200° C. to about 1000° C., for example from about 250° C. to about 800° C., including from about 250° C. to about 750° C., conveniently from about 300° C. to about 650° C., typically from about 350° C. to about 600° C. and particularly from about 350° C. to about 550° C.

Similarly, the present process can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kpaa to about 500 kpaa.

The weight hourly space velocity (WHSV), defined as the total weight of feedstock excluding any diluents per hour per weight of molecular sieve in the catalyst composition, typically ranges from about 1 $hr^{-1}$ to about 5000 $hr^{-1}$, such as from about 2 $hr^{-1}$ to about 3000 $hr^{-1}$, for example from about 5 $hr^{-1}$ to about 1500 $hr^{-1}$, and conveniently from about 10 $hr^{-1}$ to about 1000 $hr^{-1}$. In one embodiment, the WHSV is greater than 20 $hr^{-1}$ and, where feedstock contains methanol and/or dimethyl ether, is in the range of from about 20 $hr^{-1}$ to about 300 $hr^{-1}$.

Where the process is conducted in a fluidized bed, the superficial gas velocity (SGV) of the feedstock including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec. See for example U.S. patent application Ser. No. 09/708,753 filed Nov. 8, 2000, which is herein incorporated by reference.

The process of the invention is conveniently conducted as a fixed bed process, or more typically as a fluidized bed process (including a turbulent bed process), such as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in *Riser Reactor, Fluidization and Fluid-Particle Systems,* pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one practical embodiment, the process is conducted as a fluidized bed process or high velocity fluidized bed process utilizing a reactor system, a regeneration system and a recovery system.

In such a process the reactor system conveniently includes a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent(s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

In an embodiment, the amount of fresh feedstock fed as a liquid and/or a vapor to the reactor system is in the range of from 0.1 weight percent to about 99.9 weight percent, such as from about 1 weight percent to about 99 weight percent, more typically from about 5 weight percent to about 95 weight percent based on the total weight of the feedstock including any diluent contained therein. The liquid and vapor feedstocks may be the same composition, or may contain varying proportions of the same or different feedstocks with the same or different diluents.

The feedstock entering the reactor system is preferably converted, partially or fully, in the first reactor zone into a gaseous effluent that enters the disengaging vessel along with the coked catalyst composition. In the preferred embodiment, cyclone(s) are provided within the disengaging vessel to separate the coked catalyst composition from the gaseous effluent containing one or more olefin(s) within the disengaging vessel. Although cyclones are preferred, gravity effects within the disengaging vessel can also be used to separate the catalyst composition from the gaseous effluent. Other methods for separating the catalyst composition from the gaseous effluent include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

The coked catalyst composition is withdrawn from the disengaging vessel and introduced to the regeneration system. The regeneration system comprises a regenerator where the coked catalyst composition is contacted with a regeneration medium, preferably a gas containing oxygen, under conventional regeneration conditions of temperature, pressure and residence time.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550° C. to 700° C. The regeneration pressure may be in the range of from about 15 psia (103 kpaa) to about 500 psia (3448 kpaa), such as from about 20 psia (138 kpaa) to about 250 psia (1724 kPaa), including from about 25 psia (172 kPaa) to about 150 psia (1034 kpaa), and conveniently from about 30 psia (207 kpaa) to about 60 psia (414 kPaa).

The residence time of the catalyst composition in the regenerator may be in the range of from about one minute to several hours, such as from about one minute to 100 minutes. The amount of oxygen in the regeneration flue gas (i.e., gas which leaves the regenerator) may be in the range of from about 0.01 mole percent to about 5 mole percent based on the total volume of the gas. The amount of oxygen in the gas used to regenerate the coked catalyst (i.e., fresh or feed gas) is typically at least about 15 mole percent, preferably at least about 20 mole percent, and more preferably from about 20 mole percent to about 30 mole percent, based on total amount of regeneration gas fed to the regenerator.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are in disclosed U.S. Pat. No. 6,290,916 (controlling moisture), which is herein fully incorporated by reference.

The regenerated catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In one embodiment, the regenerated catalyst composition withdrawn from the regeneration system is returned to the riser reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more riser reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, *Experimental Techniques, Circulating Fluidized Beds,* Grace, Avidan and Knowlton, eds., Blackie, 1997 (336-337), which is herein incorporated by reference.

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment, for example various condensers, heat exchangers, refrigeration systems or chill trains, compressors, knock-out drums or pots, pumps, and the like.

In an alternative embodiment that can be optionally combined with the processes described above, the olefin(s) produced are directed to one or more polymerization processes for producing various polyolefins. Polymerization processes include solution, gas phase, slurry phase and a high pressure processes, or a combination thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above. However, the preferred polymerization catalysts are the Ziegler-Natta, Phillips-type, metallocene, metallocene-type and advanced polymerization catalysts, and mixtures thereof.

In a preferred embodiment, the polymerization process comprises a process for polymerizing one or more olefin(s) in the presence of a polymerization catalyst system in a polymerization reactor to produce one or more polymer products, wherein the one or more olefin(s) have been made by converting an alcohol, particularly methanol, using a molecular sieve catalyst composition as described above. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

Having now fully described this invention, it will be appreciated by those skilled in the art that the invention can be performed within a wide range of parameters within what is claimed, without departing from the spirit and scope of the invention.

We claim:

1. A process for transferring catalyst particles into an oxygenate to olefin reaction system, comprising:
    a) storing metalloaluminophosphate catalyst particles in a storage container;
    b) transferring the stored catalyst particles from the storage container to the reaction system, wherein transferring the stored catalyst particles from the storage container to the reaction system comprises pneumatically conveying the catalyst particles in a conduit from the storage container to the reaction system by a gas flow at a flow rate of at least 0.2 scf/lb catalyst; and
    c) introducing the gas flow into the storage container to transfer the stored catalyst particles at a volume transfer ratio of gas entering the storage container venus catalyst particles and gas exiting from the storage container of from 0.99 to 10.0, wherein the gas flow has a water dew point of 0° F. or less and the cumulative water content of the gas flow introduced into the storage container to transfer the catalyst is less than 0.1 lb water per lb of total catalyst.

2. The process of claim 1, wherein the gas flow is introduced into the container at a volume transfer ratio of from 1.0 to 5.0.

3. The process of claim 1, wherein the gas flow has a water dew point of −20° F. or less.

4. The process of claim 1, wherein the container is at a pressure of from 0 psig to 100 psig during transfer.

5. The process of claim 1, wherein the container is at a pressure of from 5 psig to 50 psig during transfer.

6. The process of claim 1, wherein the container is at a pressure of from 15 psig to 30 psig during transfer.

7. The process of claim 1, wherein the gas flow comprises at least one gas selected from the group consisting of air, $N_2$, helium, CO, $CO_2$, $H_2$, argon, and $O_2$.

8. The process of claim 1, wherein the catalyst particles are pneumatically conveyed by a gas flow at a flow rate of from 0.2 to 1 scf/lb catalyst.

9. The process of claim 1, wherein the catalyst particles are pneumatically conveyed by a gas flow at a flow rate of from 0.5 to 0.75 scf/lb catalyst.

10. The process of claim 1, wherein the cumulative water content of gases introduced into the storage container and gases used to pneumatically convey the catalyst is less than 0.01 lb water per lb of total catalyst transferred.

11. The process of claim 1, wherein the cumulative water content of gases introduced into the storage container and gases used to pneumatically convey the catalyst is less than 0.001 lb water per lb of total catalyst transferred.

12. The process of claim 1, wherein the cumulative water content of gases introduced into the storage container and gases used to pneumatically convey the catalyst is less than 0.0001 lb water per lb of total catalyst transferred.

13. The process of claim 1, wherein transferring the stored catalyst particles from the container to the reaction system comprises transferring the stored catalyst particles from the container to an intermediate hopper, and subsequently transferring the catalyst particles from the intermediate hopper to the reaction system.

14. The process of claim 1, wherein the gas flow introduced into the container has a relative water partial pressure of not greater than 0.1.

15. The process of claim 1, wherein the gas flow introduced into the container has a relative water partial pressure of not greater than 0.01.

16. The process of claim 1, wherein the gas flow introduced into the container has a relative water partial pressure of not greater than 0.001.

17. The process of claim 1, wherein the gas flow introduced into the container has a relative water partial pressure of not greater than 0.0001.

18. The process of claim 1, wherein the reaction system is a dense bed reaction system, fixed bed reaction system, fluidized bed reaction system, fast fluidized bed reaction system, circulating fluidized bed reaction system, or riser reactor system.

19. The process of claim 1, wherein the catalyst particles comprise a metalloaluminophosphate molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, metal containing molecular sieves thereof, and mixtures thereof.

20. The process of claim 19, wherein the activated metalloaluminophosphate molecular sieve contains Si and Al at a Si/Al ratio of not greater than 0.5.

21. The process of claim 20, wherein the activated metalloaluminophosphate molecular sieve contains Si and Al at a Si/Al ratio of not greater than 0.3.

22. The process of claim 20, wherein the activated metalloaluminophosphate molecular sieve contains Si and Al at a Si/Al ratio of not greater than 0.2.

23. The process of claim 20, wherein the activated metalloaluminophosphate molecular sieve contains Si and Al at a Si/Al ratio of not greater than 0.15.

24. The process of claim 20, wherein the activated metalloaluminophosphate molecular sieve contains Si and Al at a Si/Al ratio of not greater than 0.1.

25. A process for transferring catalyst particles within an oxygenate to olefin reaction system, comprising:
 a) storing metalloaluminophosphate catalyst particles in a container or hopper;
 b) transferring the stored catalyst particles from the container or hopper into a vessel in the reaction system;
 c) introducing a gas flow into the container or hopper during the catalyst particle transfer at a volume transfer ratio of gas entering the storage container versus catalyst particles and gas exiting from the storage container of from 0.99 to 10;
 d) monitoring at least one of the acid density and the moisture content of the catalyst particles during transfer using infrared spectroscopy;
 e) stopping the particle transfer when a monitored acid density value or a monitored moisture content value of the catalyst particles corresponds to an acid density value or moisture content value for deactivated catalyst particles.

26. The process of claim 25, wherein the catalyst particles are monitored using Diffuse Reflectance Fourier Transform infrared spectroscopy.

27. The method of claim 25, wherein the gas flow is introduced into the container or hopper during the catalyst particle transfer at a volume transfer ratio of from 1.0 to 5.

* * * * *